US008173382B2

(12) United States Patent
Mattingly et al.

(10) Patent No.: US 8,173,382 B2
(45) Date of Patent: *May 8, 2012

(54) ASSAY FOR CARDIAC TROPONIN AUTOANTIBODIES

(75) Inventors: Phillip G. Mattingly, Third Lake, IL (US); Maciej Adamczyk, Gurnee, IL (US); Roy Jeffrey Brashear, Mundelein, IL (US); Robert C. Doss, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/857,615

(22) Filed: Aug. 17, 2010

(65) Prior Publication Data

US 2010/0311079 A1 Dec. 9, 2010

Related U.S. Application Data

(62) Division of application No. 11/588,073, filed on Oct. 26, 2006, now Pat. No. 7,776,605.

(51) Int. Cl.
*G01N 31/00* (2006.01)
*G01N 33/53* (2006.01)

(52) U.S. Cl. ............... 435/7.93; 435/7.1; 436/8; 436/10; 436/175; 436/506; 436/518; 436/523; 436/524; 436/528; 436/540

(58) Field of Classification Search ............... 435/6, 7.1, 435/7.9, 287.2; 436/506, 513, 514, 517, 436/518, 523, 524, 526, 528, 536, 538, 540, 436/8, 10, 175, 811; 422/430, 82.05, 82.09
See application file for complete search history.

(56) References Cited

U.S. PATENT DOCUMENTS

| 3,817,837 A | 6/1974 | Rubenstein et al. |
| 3,850,752 A | 11/1974 | Schuurs et al. |
| 3,939,350 A | 2/1976 | Kronick et al. |

(Continued)

FOREIGN PATENT DOCUMENTS

EP 273115 A2 7/1988

(Continued)

OTHER PUBLICATIONS

Eriksson et al. Negative Interference in Cardiac Troponin I Immunoassays by Circulating Troponin Autoantibodies, Clinical Chemistry 51 (5): 839-847 (Feb. 1, 2005).*

(Continued)

*Primary Examiner* — Gail R Gabel
(74) *Attorney, Agent, or Firm* — Audrey L. Bartnicki; Emily Haliday, Weaver, Austin, Villeneuve & Sampson LLP

(57) ABSTRACT

The invention provides among other things methods and kits based on assaying for cardiac troponin autoantibodies, either in conjunction with an assay for cardiac troponin and/or as an independent indicator of cardiac pathology, such as myocarditis, cardiomyopathy, and/or ischemic heart disease. Assay methods of the invention can be employed among other things to identify cardiac pathology, or risk thereof, in subjects who have an autoimmune disease or who are related to an individual with an autoimmune disease. In particular embodiments, the invention also provides a method of determining whether a subject having, or at risk for, a cardiac pathology is a candidate for immunosuppressive therapy or immunoabsorption therapy. The invention also provides kits and kit components that are useful for performing the methods of the invention.

26 Claims, 12 Drawing Sheets

U.S. PATENT DOCUMENTS

| | | | |
|---|---|---|---|
| 3,996,345 | A | 12/1976 | Ullman et al. |
| 4,275,149 | A | 6/1981 | Litman et al. |
| 4,277,437 | A | 7/1981 | Maggio |
| 4,366,241 | A | 12/1982 | Tom et al. |
| 4,637,880 | A | 1/1987 | Halbert |
| 4,956,778 | A | 9/1990 | Naito |
| 5,006,309 | A | 4/1991 | Khalil et al. |
| 5,063,081 | A | 11/1991 | Cozzette et al. |
| 5,089,424 | A | 2/1992 | Khalil et al. |
| 5,091,513 | A | 2/1992 | Huston et al. |
| 5,132,405 | A | 7/1992 | Huston et al. |
| 5,244,630 | A | 9/1993 | Khalil et al. |
| 5,534,615 | A | 7/1996 | Baker et al. |
| 5,561,049 | A | 10/1996 | Vold et al. |
| 5,741,654 | A | 4/1998 | Michel et al. |
| 5,795,725 | A | 8/1998 | Buechler et al. |
| 5,981,180 | A | 11/1999 | Chandler et al. |
| 6,174,686 | B1* | 1/2001 | Buechler et al. ............... 435/7.1 |
| 6,309,888 | B1 | 10/2001 | Holvoet et al. |
| 6,537,760 | B1 | 3/2003 | Bergmann et al. |
| 6,670,115 | B1 | 12/2003 | Zhang |
| 6,682,648 | B1 | 1/2004 | MacPhee et al. |
| 6,887,714 | B2 | 5/2005 | Fritsch et al. |
| 6,896,872 | B2 | 5/2005 | Dambinova |
| 7,045,310 | B2 | 5/2006 | Buck, Jr. et al. |
| 7,045,364 | B2 | 5/2006 | Limoges et al. |
| 7,064,189 | B2 | 6/2006 | Salcedo et al. |
| 7,196,169 | B2* | 3/2007 | Van Eyk et al. ............... 530/350 |
| 7,258,994 | B2 | 8/2007 | Vojdani |
| 7,285,418 | B2 | 10/2007 | Katrukha et al. |
| 7,348,157 | B2 | 3/2008 | Eriksson et al. |
| 7,407,767 | B2 | 8/2008 | Honjo et al. |
| 7,776,605 | B2* | 8/2010 | Mattingly et al. ............... 436/8 |
| 2003/0100036 | A1 | 5/2003 | Vojdani |
| 2003/0170881 | A1 | 9/2003 | Davis et al. |
| 2004/0018577 | A1 | 1/2004 | Emerson Campbell et al. |
| 2004/0091934 | A1 | 5/2004 | Narvanen et al. |
| 2004/0219538 | A1* | 11/2004 | Chou et al. ............... 435/6 |
| 2004/0219604 | A1 | 11/2004 | Eriksson et al. |
| 2005/0054078 | A1 | 3/2005 | Miller et al. |
| 2005/0181451 | A1 | 8/2005 | Bates |
| 2006/0024744 | A1 | 2/2006 | Mills et al. |
| 2006/0024749 | A1 | 2/2006 | Dambinova |
| 2006/0040288 | A1 | 2/2006 | Richardson et al. |
| 2006/0094056 | A1 | 5/2006 | Chappell et al. |
| 2006/0160164 | A1 | 7/2006 | Miller et al. |
| 2006/0246525 | A1 | 11/2006 | Honjo |
| 2007/0012888 | A1 | 1/2007 | Bichay |
| 2007/0037227 | A1 | 2/2007 | Hanash et al. |
| 2007/0172888 | A1 | 7/2007 | Hallermayer et al. |
| 2008/0305512 | A1 | 12/2008 | Mattingly et al. |
| 2009/0017560 | A1 | 1/2009 | Adamczyk et al. |
| 2009/0246800 | A1 | 10/2009 | Mattingly et al. |

FOREIGN PATENT DOCUMENTS

| | | |
|---|---|---|
| EP | 326100 A2 | 8/1989 |
| EP | 425633 A1 | 1/1990 |
| EP | 0425633 B1 | 4/1990 |
| EP | 406473 A1 | 1/1991 |
| EP | 0424634 A2 | 5/1991 |
| EP | 0273115 B1 | 9/1994 |
| EP | 0424634 B1 | 6/1995 |
| EP | 0406473 B1 | 9/1995 |
| EP | 0326100 B1 | 9/1996 |
| EP | 1149914 | 10/2001 |
| EP | 1271152 A1 | 1/2003 |
| EP | 1473567 A1 | 11/2004 |
| EP | 1619498 A2 | 1/2006 |
| EP | 1473567 B1 | 7/2006 |
| WO | WO9963345 A1 | 12/1999 |
| WO | WO03016575 A1 | 2/2003 |
| WO | 2004091476 A1 | 10/2004 |
| WO | WO2006043891 A1 | 4/2006 |
| WO | 2007085411 A1 | 8/2007 |
| WO | WO2008051761 A2 | 5/2008 |
| WO | WO2008051762 A2 | 5/2008 |

OTHER PUBLICATIONS

Eriksson et al. (Autoantibodies against Cardiac Troponins, The New England Journal of Medicine 352 (1): 98-100 (Jan. 6, 2005)).*
Eriksson et al. (Coomparison of Cardiac Troponin I Immunoassays Variably Affected by Circulating Autoantibodies, Clinical Chemistry 51 (5): 848-855 (Feb. 1, 2005)).*
Adamczyk, et al., "Circulating Cardiac Troponin-I Autoantibodies in Human Plasma and Serum", Contemporary Challenges in Autoimmunity, 1173, 67-74 (2009).
Shmilovich et al., "Autoantibodies to cardiac troponin I in patients with idiopathic dilated and ischemic cardiomyopathy", International Journal of Cardiology, 117 (2) 198-203 (2006).
ISA/EP Extended European Search Report for EP Application No. 07871173.6-2404 dated Dec. 2, 2009.
Bohner, et al., Clin. Chem., vol. 42 (1996), pp. 2046.
Bui, et al., American Heart Journal, vol. 131, No. 4 (1996), pp. 663-667.
Caforio, et al., G Ital. Cardiol, vol. 27 (1997), pp. 106-112.
Dighiero, et al., Clin Exp Immunol, vol. 82 (1990), pp. 52-56.
Eriksson, et al., Cinical BioChem., vol. 37 (2004), pp. 472-480.
Eriksson, et al., Cinical Chemistry, vol. 49 (2003), pp. 1095-1104.
Eriksson, et al., Cinical Chemistry, vol. 50 (2004), pp. 1101-1102.
Eriksson, et al., Cinical Chemistry, vol. 51 (2005), pp. 1755-1756.
Eriksson, et al., Cinical Chemistry, vol. 51 (2005), pp. 839-847.
Eriksson, et al., Cinical Chemistry, vol. 51 (2005), pp. 848-855.
Eriksson, et al., New England Journal of Medicine, vol. 352 (2005), pp. 98-100.
Filippantos, et al., Heart Fall Rev., vol. 12, (2007), pp. 87-90.
Frostegard, Arterioscler Thromb. Vasc. Biol., vol. 25 (2005), pp. 18-28.
Goser, et al. Criculation, vol. 114 (2006), pp. 1693-1702.
Haralambous, et al., Autoimmunity, vol. 20 (1995), pp. 267-275.
Kenny, et at., Journal of Rheumatology, vol. 32 (2005), pp. 1258-1261.
Koga, et al., Journal of Immunology Methods, vol. 105 (1987), pp. 15-21.
Leuschner, et al., European Heart Journal, vol. 29 (2008), pp. 1949-1955.
Maisch, et al., Herz, vol. 30, No. 6 (2005), pp. 535-544.
Okazaki, et al., Nat Med, vol. 9 (2003), pp. 1477-1483.
Okazaki, et al., Trends Mol. Med., vol. 11 (2005), pp. 322-326.
Panteghini, Clinical Chemistry, vol. 51 (2005), pp. 803-804.
Scherer, et al., Cardiology, vol. 95 (2001), pp. 20-24.
Takaya, et al., Tokai Journal Exp. Clin. Med., vol. 17 (1992), pp. 35-39.
Takeda, et al., Int. J Mol. Med., vol. 11 (2003), pp. 13-16.
Wu, Circulation, vol. 114 (2006), pp. 1673-1675.
Zammanou, et al., J clin Lab Anal, vol. 16 (2002), pp. 194-201.
International Searching Authority/United States, International Search Report for PCT/US2007/81606, Sep. 9, 2008.
Åkerström B., et al., "Protein G: A Powerful Tool for Binding and Detection of Monoclonal and Polyclonal Antibodies," The Journal of Immunology, 1985, vol. 135 (4), pp. 2589-2592.
Asai D.J., "Antibodies in Cell Biology" in: Methods in Cell Biology, vol. 37, Academic Press Inc., 1993, Table of Contents.
Barnes D., et al., "Serum-Free Cell Culture: A Unifying Approach," Cell, 1980, vol. 22 (3), pp. 649-655, Table of Contents.
Butler, et al."Mammalian Cell Biotechnology—A Practical Approach",1991,272,1-8.
Caforio A.L., et al., "Circulating Cardiac Autoantibodies in dilated Cardiomyopathy and Myocarditis: pathogenetic and Clinical significance," The European Journal of Heart Failure, 2002, vol. 4, pp. 411-417.
Caforio, et al., "Autoimmune Myocarditis and Dilated Cardiomyopathy: Focus on Cardiac Auto Antibodies," Lupus, 2005, vol. 14, pp. 652-655.
Clackson T., et al., "Making Antibody Fragments Using Phage Display Libraries," Nature, 1991, vol. 352, pp. 624-628.
Cohen S.N., et al., "Non Chromosomal Antibiotic Resistance in Bacteria: Genetic Transformationof Escherichia coli by R-Factor DNA," Proceedings of the National Academy of Sciences, 1972, vol. 69 (8), pp. 2110-2114.

Coligan J.E., et al., "Peptides" in: Current Protocols in Immunology, John Wiley & Sons, 1991.

Dennis M.S., et al., "Binding Interactions of Kistrin With Platelet Glycoprotein IIb-IIIa: Analysis by Site-Directed Mutagenesis," Proteins, 1993, vol. 15 (3), pp. 312-321.

Gorman C.M., et al., "Transient Production of Proteins Using an Adenovirus Transformed Cell Line", DNA and Protein Engineering Technologies, 1990, 2 (1), 3-10.

Griffiths A.D., et al., "Human Anti-Self Antibodies with High Specificity from Phage Display Libraries," European Molecular Biology Organization Journal, 1993, vol. 12 (2), pp. 725-734.

Gürlek A., et al., "Association Between Anticardiolipin Antibodies and Recurrent Cardiac Events in Patients with Acute Coronary Syndrome," International Heart Journal, 2005, vol. 46 (4), pp. 631-638.

Hoogenboom H.B., et al., "Multi-Subunit Proteins on the Surface of Filamentous Phage: Methodologies for Displaying Antibody (Fab) Heavy and Light Chains," Nucleic Acids Research, 1991, vol. 19 (15), pp. 4133-4137.

Huston J.S., et al., "Protein Engineering of Antibody Binding Sites: Recovery of Specific Activity in an Anti-Digoxin Single-Chain Fv Analogue Produced in *Escherichia coli*," Proceedings of the National Academy of Sciences of the USA, 1988, vol. 85, pp. 5879-5883.

International Preliminary Report on Patentabiligy and Written Opinion for Application No. PCT/US07/081608, mailed on May 7, 2009, 8 pages.

International Preliminary Report on Patentability and Written Opinion for Application No. PCT/US07/088477, mailed on Jul. 2, 2009, 4 pages.

International Preliminary Report on Patentability and Written Opinion for Application No. PCT/US2007/081606, mailed on May 7, 2009, 4 pages.

International Search Report and Written Opinion for Application No. PCT/US07/081608, mailed on May 27, 2008, 14 pages.

International Search Report and Written Opinion for for Application No. PCT/US07/088477, mailed on Aug. 5, 2008, 9 pages.

Jahns R., et al., "$\beta_1$-Adrenergic Receptor Function, Autoimmunity, and Pathogenesis of Dilated Cardiomyopathy," Trends in Cardiovascular Medicine , 2006, vol. 16 (1), pp. 20-24.

Janeway, et al., "Immunobiology," 3rd edition, 1997, Three pages, including p. 2:9, 2:10 and 2:32.

Kohler G., et al., "Continuous Cultures of Fused Cells Secreting Antibody of Predefined Specificity ," Nature, 1975, vol. 256 (5517), pp. 495-497.

Kronvall G., "A Surface Component in Group A, C, and G Streptococci with Non-Immune Reactivity for Immunoglobulin G," Journal of Immunology, 1973, vol. 111 (5), pp. 1401-1406.

Liao Y.H., et al., "Autoantibodies against the $\alpha_1$-Adrenoceptor Related with the Increased Stroke Recurrence in Hypertensive Patients," Circulation, 2005, 112 (17), pp. 346.

Luther P., et al., "$\alpha_1$-Adrenergic Receptor Antibodies in Patients With Primary Hypertension," Hypertension, 1997, vol. 29, pp. 678-682.

Marks J.D., et al., "By-passing Immunization: Human Antibodies from V-gene Libraries Displayed on Phage," Journal of Molecular Biology, 1991, vol. 222, pp. 581-597.

Marks J.D., et al., "By-Passing Immunization: Building High Affinity Human Antibodies by Chain Shuffling," Biotechnology, 1992, vol. 10, pp. 779-783.

Mather Jennie P., "Mammalian Cell Culture", The Use of Serum-Free Hormone-Supplemented Media, 1984,1-9, Table of Contents.

Matsui S., et al., "Dilated Cardiomyopathy Defines Serum Autoantibodies Against G-Protein-Coupled Cardiovascular Receptors," Autoimmunity, 1995, vol. 21 (2), pp. 85-88.

McCafferty J., et al., "Phage Antibodies: Filamentous Phage Displaying Antibody Variable Domains," Nature, 1990, vol. 348, pp. 552-554.

Merrifield R.B., et al., "Solid Phase Peptide Synthesis. I. The Synthesis of a Tetrapeptide," Journal of the American Chemical Society, 1963, vol. 85 (14), pp. 2149-2154.

Michels V.V., et al, "Circulating Heart Autoantibodies in Familial as Compared With Nonfamilial Idiopathic Dilated Cardiomyopathy," Mayo Clinic Proceedings, 1994, vol. 69 (1), pp. 24-27.

Quintana F.J., et al., "Antigen microarrays identify unique serum autoantibody signatures in clinical and pathologic subtypes of multiple sclerosis," Proceedings of the National Academy of Sciences, 2008, vol. 105 (48), pp. 18889-18894.

Stewart J.M., et al., Solid-Phase Peptide Synthesis, 2nd Edition, Pierce Chemical Company, 1984, Table of Contents.

Stites D.P., et al., eds., "Basic and Clinical Immunology", 7th Edition, Appleton & Lange, 1991, Table of Contents.

Supplementary European Search Report for Application No. EP07869697, mailed on Jun. 24, 2010, 9 pages.

Vaitukaitis J.L., "Production of Antisera with Small Doses of Immunogen: Multiple Intradermal Injections," Methods in Enzymology, 1981, vol. 73 (Pt B), pp. 46-52.

Zhang Lin, et al., "Study of autoantibodies against G-protein-coupled $\beta_2$- and $\alpha_1$-adrenergic and angiotensis II type 1 receptors in patients with dilated cardiomyopathy", Journal of Oncology, 2002, vol. 30, pp. 363-365, Abstract.

Zhang Lin, et al., "Study of autoantibodies against G-protein-coupled $\beta_2$- and $\alpha_1$-adrenergic and angiotensin II-1 receptors in patients with chronic heart failure", Journal of Oncology, 2003, 31, 17-20, Abstract.

Zhong M., et al., "Distribution and Biological Effects of Autoantibody Against $\alpha_1$-Adrenoceptor in Patients with Primary Hypertension," Circulation, 2006, 114 (18), pp. 494.

\* cited by examiner

ASSAY FOR CARDIAC TROPONIN AUTOANTIBODIES

CROSS-REFERENCE TO RELATED APPLICATIONS

This application is a divisional of U.S. patent application Ser. No. 11/588,073 filed on Oct. 26, 2006, now U.S. Pat. No. 7,776,605; which is incorporated herein by reference.

FIELD OF THE INVENTION

The present invention relates generally to the area of assays for autoantibodies reactive with a cardiac troponin. In particular, the invention relates among other things to the use of such assays and kits for such assays in the assessment of cardiac pathologies or the risk thereof.

BACKGROUND OF THE INVENTION

Troponin complex is a heteromeric protein playing an important role in the regulation of skeletal and cardiac muscle contraction. It consists of three subunits: troponin I (TnI), troponin T (TnT) and troponin C (TnC). Each subunit is responsible for part of troponin complex function; e.g., TnI inhibits the ATP-ase activity of acto-myosin.

TnT and TnI are present in myocardium in different forms than in skeletal muscles. Cardiac TnI (cTnI) is expressed only in myocardium. cTnI has been widely used as a marker of cardiac tissue injury. cTnI is considered to be more sensitive and significantly more specific in the diagnosis of myocardial infarction than CK-MB, myoglobin, and LDH isoenzymes.

cTnI can be detected in patient's blood 3-6 hours after onset of the chest pain, reaching peak level within 16-30 hours. cTnI is also useful for the late diagnosis of acute myocardial infarction, because elevated concentrations can be detected in blood even 5-8 days after onset.

During the incubation in the necrotic muscle after acute myocardial infarction, cTnI is cleaved by endogenous proteases. The most stable fragment resulting from this cleavage is located between 30 and 110 amino acid residues. For this reason, cTnI assays have employed antibodies that recognize this fragment.

In view of the importance of early detection of cardiac tissue injury, there clearly remains a need for methods and kits to identify cardiac pathology, or risk thereof, either as an independent indicator, or which can be employed in conjunction with other assays.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

The invention provides among other things assays for autoantibodies reactive with a cardiac troponin, kits for performing such assays, and the use of such assays and kits in the assessment of cardiac pathologies or the risk thereof.

In one embodiment, the present invention provides a method of determining the reliability of a cardiac troponin assay result, e.g., where there is a chance that the amount of cardiac troponin measured by assay is impacted by the presence of autoantibodies reactive with a cardiac troponin within a subject. The method entails assaying a biological sample for an autoantibody reactive with a cardiac troponin, wherein the presence of an elevated level of cardiac troponin-reactive autoantibody indicates that the cardiac troponin assay result is not reliable. This method optionally comprises the steps of: (a) obtaining a biological sample from the subject; (b) determining the level of autoantibody reactive with a cardiac troponin in the sample (e.g., using a cardiac troponin antigen); and (c) evaluating the reliability of a cardiac troponin assay result based on the level of autoantibody reactive with a cardiac troponin in the sample.

In another embodiment, the invention provides methods of assessing risk of a cardiac pathology. This method entails assaying a biological sample for an autoantibody reactive with a cardiac troponin, wherein the presence of an elevated level of cardiac troponin-reactive autoantibody indicates an elevated risk of a cardiac pathology. This method optionally comprises the steps of: (a) obtaining a biological sample from a subject; (b) determining the level of autoantibody reactive with a cardiac troponin in the sample (e.g., using a cardiac troponin antigen); and (c) evaluating the risk of a cardiac pathology result based on the level of autoantibody reactive with a cardiac troponin in the sample.

In a variation of this embodiment, a method of the invention entails assaying a biological sample for a cardiac troponin, and assaying a biological sample from the subject for an autoantibody reactive with a cardiac troponin. The assays can be conducted using one biological sample or different ones. The presence of an elevated level of cardiac troponin and/or an elevated level of cardiac troponin-reactive autoantibody indicates an elevated risk of a cardiac pathology. This method optionally comprises the steps of: (a) obtaining one or more biological samples from a subject; (b) determining the level of a cardiac troponin in the one or more biological samples (e.g., using an antibody specific for the cardiac troponin antigen); (c) determining the level of autoantibody reactive with a cardiac troponin in the one or more biological samples (e.g., using a cardiac troponin antigen); and (d) evaluating the risk of a cardiac pathology result based on the presence of an elevated level of cardiac troponin and/or an elevated level of autoantibody reactive with a cardiac troponin in the sample. In this method, step (c) can be done before, after, concurrent with, or in the absence of step (b), optionally on either the same or a different biological sample.

In particular embodiments, the above-described methods, and other methods described herein can be carried out using a biological sample obtained from a subject with chest pain. In certain embodiments, the subject is suspected of having a myocardial infarction.

Methods of assessing risk of cardiac pathology include screening for a subject having, or at risk of having, myocarditis, cardiomyopathy, and ischemic heart disease. This method entails assaying a biological sample from the subject for an autoantibody reactive with a cardiac troponin. The presence of an elevated level of cardiac troponin-reactive autoantibody indicates the presence of, or risk of, the cardiac pathology. This method optionally comprises the steps of: (a) obtaining a biological sample from a subject; (b) determining the level of autoantibody reactive with a cardiac troponin in the sample (e.g., using a cardiac troponin antigen); and (c) evaluating the risk of a cardiac pathology result based on the level of autoantibody reactive with a cardiac troponin in the sample.

The invention also provides a method of determining whether a subject having, or at risk for, a cardiac pathology is a candidate for immunosuppressive therapy and/or immunoabsorption therapy. The method entails assaying a biological sample from the subject for an autoantibody reactive with a cardiac troponin. The presence of an elevated level of cardiac troponin-reactive autoantibody indicates that the subject is a candidate for such therapy. This method optionally comprises the steps of: (a) obtaining a biological sample from a subject; (b) determining the level of autoantibody reactive with a cardiac troponin in the sample (e.g., using a cardiac troponin antigen); and (c) evaluating whether a subject is a candidate for immunosuppressive therapy and/or immunoabsorption therapy based on the level of autoantibody reactive with a cardiac troponin in the sample.

In another embodiment, the invention provides a method of identifying a subject having, or at risk for, a cardiac pathology. The method entails assaying a biological sample from the subject for an autoantibody reactive with a cardiac troponin, wherein the subject has an autoimmune disease, or the subject is a first-degree relative of an individual having an autoimmune disease. This method optionally comprises the steps of: (a) obtaining a biological sample from a subject, wherein the subject has an autoimmune disease, and/or is a first-degree relative of an individual having an autoimmune disease; (b) determining the level of autoantibody reactive with a cardiac troponin in the sample (e.g., using a cardiac troponin antigen); and (c) evaluating the risk of a cardiac pathology result based on the level of autoantibody reactive with a cardiac troponin in the sample.

In each of the methods described herein: the biological sample can be obtained from a subject that is a mammal (e.g., optionally human); the cardiac troponin assayed can include a cardiac troponin selected from the group consisting of a cardiac troponin I, T, C, and complexes thereof; and the autoantibody can be reactive with a cardiac troponin comprising a cardiac troponin selected from the group consisting of a cardiac troponin I, T, C, and complexes thereof.

Any of the methods described herein can conveniently be carried out using an immunoassay. Suitable immunoassays include agglutination assay. In an exemplary agglutination assay, a biological sample is contacted with a cardiac troponin antigen affixed to a solid phase, under conditions sufficient for binding of the cardiac troponin antigen to any cardiac troponin-reactive autoantibody present in the sample, followed by measurement of any agglutination of the sample. The degree of agglutination is positively correlated with the concentration of cardiac troponin-reactive autoantibody present in the sample.

In other embodiments, the biological sample is contacted with a cardiac troponin antigen, under conditions sufficient for binding of the cardiac troponin antigen to any cardiac troponin-reactive autoantibody present in the sample, and signal is detected from one or more complex(es) comprising the cardiac troponin antigen bound to cardiac troponin-reactive autoantibody. Such immunoassays can be carried out in a non-competitive format, in which case the signal is positively correlated with the concentration of any cardiac troponin-reactive autoantibody present in the sample.

In exemplary non-competitive immunoassays useful in the invention, the method additionally entails contacting the biological sample with a species-specific antibody, wherein the species-specific antibody is specific for the species from which the biological sample was obtained, under conditions sufficient for specific binding of the species-specific antibody to any cardiac troponin-reactive autoantibody present. Signal detection entails detecting any complex including the cardiac troponin antigen bound to cardiac troponin-reactive autoantibody, which is itself bound to labeled species-specific antibody. The contact between the biological sample and the cardiac troponin antigen and the contact between the biological sample and the species-specific antibody can be carried out simultaneously or sequentially, in any order.

In exemplary non-competitive immunoassays useful in the invention, the cardiac troponin antigen can be affixed to a solid phase. Binding of the cardiac troponin to any cardiac troponin-reactive autoantibody present in the sample forms a solid phase-affixed complex, and signal is detected from this complex. If desired, the species-specific antibody can be labeled (e.g., in a sandwich immunoassay). Alternatively, the species-specific antibody can be affixed to a solid phase. In this case, binding of the species-specific antibody to any cardiac troponin-reactive autoantibody present in the sample forms a solid phase-affixed complex, and signal is detected from this complex. If desired, the cardiac troponin antigen can be labeled (e.g., in a sandwich immunoassay).

Immunoassays useful in the invention can also be carried out in a competitive format, in which case the signal is negatively correlated with the concentration of cardiac troponin-reactive autoantibody present in the sample. In particular embodiments, the biological sample is contacted with a cardiac troponin antigen, under conditions sufficient for binding of the cardiac troponin antigen to any cardiac troponin-reactive autoantibody present in the sample. In addition the biological sample is contacted with a labeled cardiac troponin-reactive antibody under conditions sufficient for specific binding of the labeled cardiac troponin-reactive antibody to the cardiac troponin antigen. The contact between the biological sample and the cardiac troponin antigen and the contact between the biological sample and the labeled cardiac troponin-reactive antibody can be carried out simultaneously or sequentially, in any order.

In exemplary competitive immunoassays useful in the invention, the cardiac troponin antigen can be affixed to a solid phase. Binding of the cardiac troponin to any cardiac troponin-reactive autoantibody present in the sample forms a solid phase-affixed complex, and signal is detected from this complex.

The invention also provides a test kit for assaying a biological sample for cardiac troponin-reactive autoantibodies. In particular embodiments, the test kit includes an antibody reactive with cardiac troponin. For example, the test kit can include a humanized monoclonal antibody, wherein the humanized monoclonal antibody is specific for a cardiac troponin. Alternatively or additionally, the test kit can include a labeled non-human monoclonal antibody, wherein the non-human monoclonal antibody is specific for a cardiac troponin.

Test kits accordingly to the invention can include, if desired, a solid phase and a capture agent affixed to the solid phase. In exemplary embodiments, the capture agent is a cardiac troponin antigen or a species-specific antibody, wherein the species-specific antibody is specific for the species from which the biological sample is to be obtained. In particular embodiments, the species-specific antibody comprises a human-specific antibody.

Alternatively or additionally, test kits according to the invention can include a labeled detection agent wherein: (1) if the capture agent is a cardiac troponin antigen, the detection agent is a species-specific antibody; and (2) if the capture agent is a species-specific antibody, the detection agent is a cardiac troponin antigen.

Suitable solid phases useful in the methods and test kits of the invention can include, for example, a microplate, an electrode, or a microparticle. Suitable microparticles can be magnetic or paramagnetic. Labels useful in the methods and test kits of the invention include direct and indirect labels. For example, acridinium-9-carboxamide can be used as a direct label. In some embodiments, signal is detected by contacting the label with an indicator reagent.

BRIEF DESCRIPTION OF THE DRAWINGS

FIG. 1 shows the chemiluminescent profiles for cTnIC concentrations of 0 ng/mL (solid diamonds), 80 ng/mL (solid squares), 400 ng/mL (solid triangles), 2000 ng/mL ("x" symbols), and 10,000 ng/mL (asterisks).

DETAILED DESCRIPTION

Figure 1:
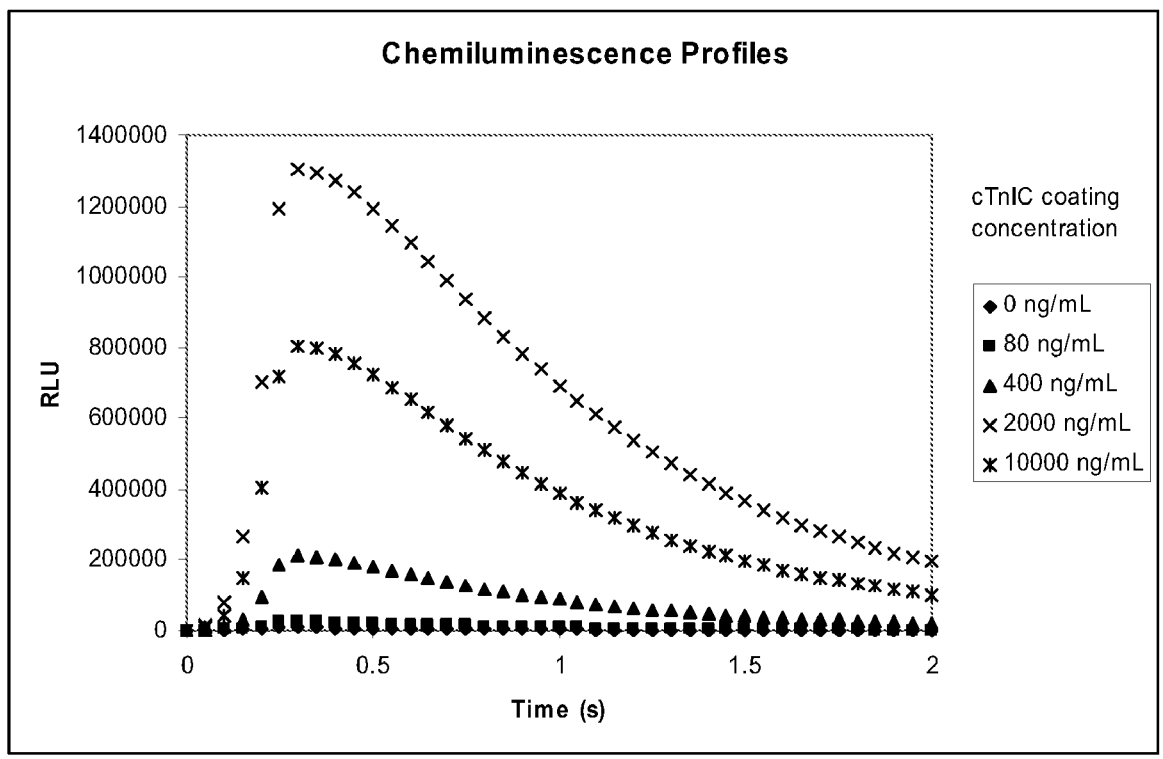
FIG. 1 is a graph of cTnIC coating concentration effect on chemiluminescence signal profile as described in Example 1.

Cardiac troponin-reactive autoantibodies may arise via molecular mimicry of pathogens such as viruses, bacteria, or toxins, genetic abnormalities, tissue damage or idiopathies. The presence of such autoantibodies leads to inflammatory processes which result in damage to cardiac tissue affecting normal cardiac function. Further, cardiac troponin-reactive autoantibodies provide an early indicator of risk for developing clinical manifestations of cardiac pathologies. Independently, cardiac troponin-reactive autoantibodies may interfere with the measurement of cTnI, for example, using conventional midfragment-specific immunoassays. This interference by endogenous antibodies can produce false negative results, such that individuals fail to be diagnosed in a timely fashion for acute myocardial infarction (AMI). The present invention includes methods based on the measurement of cardiac troponin autoantibodies, in conjunction with cardiac troponin and as an independent indicator of cardiac pathology.

Definitions

Unless specifically defined otherwise as follows, all technical, scientific, and other terms used herein have the same meaning as commonly understood by one of ordinary skill in the art to which this invention belongs.

The following terms encompass polypeptides that are identified in Genbank by the following designations, as well as polypeptides that are at least about 70% identical to polypeptides identified in Genbank by these designations: cardiac troponin I, cardiac troponin T, cardiac troponin C. In alternative embodiments, these terms encompass polypeptides identified in Genbank by these designations and polypeptides sharing at least about 80, 90, 95, 96, 97, 98, or 99% identity. Percent identity can, for example, be determined by a sequence alignment performed using BLASTP with default parameters set to measure the selected percent identity. In particular embodiments, these terms encompass full-length polypeptides, as well as fragments thereof.

As used herein, the term "cardiac troponin antigen" refers to any cardiac troponin or fragment or complex thereof that is capable of binding to an antibody specific for a cardiac troponin or cardiac troponin complex.

The term "cardiac pathology" refers to any deviation from a healthy or normal condition of the heart, including any structural or functional abnormality of the heart, or of the blood vessels supplying the heart, that impairs its normal functioning. Examples of cardiac pathologies include myocarditis, cardiomyopathy, and ischemic heart disease.

The term "myocarditis" refers to inflammation of the myocardium. Myocarditis can be caused by a variety of conditions such as viral infection, sarcoidosis, rheumatic fever, autoimmune diseases (such as systemic lupus, etc.), and pregnancy.

The term "cardiomyopathy" refers to a weakening of the heart muscle or a change in heart muscle structure. It is often associated with inadequate heart pumping or other heart function abnormalities. Cardiomyopathy can be caused by viral infections, heart attacks, alcoholism, long-term, severe high blood pressure, nutritional deficiencies (particularly selenium, thiamine, and L-carnitine), systemic lupus erythematosus, celiac disease, and end-stage kidney disease. Types of cardiomyopathy include dilated cardiomyopathy, hypertrophic cardiomyopathy, and restrictive cardiomyopathy.

As used herein, the term "dilated cardiomyopathy" refers to a global, usually idiopathic, myocardial disorder characterized by a marked enlargement and inadequate function of the left ventricle. Dilated cardiomyopathy includes ischemic cardiomyopathy, idiopathic cardiomyopathy, hypertensive cardiomyopathy, infectious cardiomyopathy, alcoholic cardiomyopathy, toxic cardiomyopathy, and peripartum cardiomyopathy.

As used herein, the term "hypertrophic cardiomyopathy" refers to a condition resulting from the right and left heart muscles growing to be different sizes.

As used herein, the term "restrictive cardiomyopathy" refers to a condition characterized by the heart muscle's inability to relax between contractions, which prevents it from filling sufficiently.

The term "ischemic heart disease" refers to any condition in which heart muscle is damaged or works inefficiently because of an absence or relative deficiency of its blood supply; most often caused by atherosclerosis, it includes angina pectoris, acute myocardial infarction, and chronic ischemic heart disease.

"Angina pectoris" refers to chest discomfort caused by inadequate blood flow through the blood vessels (coronary vessels) of the myocardium.

A "myocardial infarction" (heart attack) occurs when an area of heart muscle dies or is damaged because of an inadequate supply of oxygen to that area.

The term "immunosuppressive therapy" is used herein to denote any therapy aimed at decreasing the body's immune response, such as, for example, the production of autoantibodies.

As used herein, the term "immunoadsorption therapy" refers to any treatment that removes antibodies from plasma by binding the target antibodies. Typically, plasma is removed from a subject, contacted with a solid phase-affixed binding partner for the target antibodies under conditions sufficient for binding, followed by return of the plasma to the subject.

As used herein, the term "autoimmune disease" refers to pathological autoimmunity. "Autoimmunity" refers to one or more immune responses directed against host antigens, characterized, for example, by the presence of autoantibodies or T lymphocytes reactive with host antigens.

A "first degree relative" is either a parent, child, or sibling.

"Biological samples" that can be assayed using the methods of the present invention include biological fluids, such as whole blood, serum, plasma, synovial fluid, cerebrospinal fluid, bronchial lavage, ascites fluid, bone marrow aspirate, pleural effusion, urine, as well as tumor tissue or any other bodily constituent or any tissue culture supernatant that could contain the analyte of interest.

"Analyte," as used herein, refers to the substance to be detected, which may be present in the biological sample. The analyte can be any substance for which there exists a naturally occurring specific binding partner or for which a specific binding partner can be prepared. Thus, an analyte is a substance that can bind to one or more specific binding partners in an assay.

A "binding partner," as used herein, is a member of a binding pair, i.e., a pair of molecules wherein one of the molecules binds to the second molecule. Binding partners that bind specifically are termed "specific binding partners." In addition to the antigen and antibody binding partners commonly used in immunoassays, other specific binding partners can include biotin and avidin, carbohydrates and lectins, complementary nucleotide sequences, effector and receptor molecules, cofactors and enzymes, enzyme inhibitors and enzymes, and the like. Furthermore, specific binding partners can include partner(s) that is/are analog(s) of the original specific binding partner, for example, an analyte-analog. Immunoreactive specific binding partners include antigens, antigen fragments, antibodies and antibody fragments, both monoclonal and polyclonal, and complexes thereof, including those formed by recombinant DNA methods.

The term "specific binding" is defined herein as the preferential binding of binding partners to another (e.g., two polypeptides, a polypeptide and nucleic acid molecule, or two nucleic acid molecules) at specific sites. The term "specifically binds" indicates that the binding preference (e.g., affinity) for the target molecule/sequence is at least 2-fold, more preferably at least 5-fold, and most preferably at least 10- or 20-fold over a non-specific target molecule (e.g. a randomly generated molecule lacking the specifically recognized site(s)).

As used herein with reference to cardiac troponin or cardiac troponin-reactive autoantibody, the term "elevated level" refers to a level in a biological sample that is higher than a normal level or range. The normal level or range for cardiac troponin and cardiac troponin-reactive autoantibody is defined in accordance with standard practice. Thus, the level measured in a particular biological sample will be compared with the level or range of levels determined in similar samples of normal tissue. In this context, "normal tissue" is tissue from an individual with no detectable cardiac pathology. The level of an analyte is said to be "elevated" where the analyte is normally undetectable (e.g., the normal level is zero), but is detected in a test sample, as well as where the analyte is present in the test sample at a higher than normal level.

A "solid phase," as used herein, refers to any material that is insoluble, or can be made insoluble by a subsequent reaction. The solid phase can be chosen for its intrinsic ability to attract and immobilize a capture agent. Alternatively, the solid phase can have affixed thereto a linking agent that has the ability to attract and immobilize the capture agent. The linking agent can, for example, include a charged substance that is oppositely charged with respect to the capture agent itself or to a charged substance conjugated to the capture agent. In general, the linking agent can be any binding partner (preferably specific) that is immobilized on (attached to) the solid phase and that has the ability to immobilize the capture agent through a binding reaction. The linking agent enables the indirect binding of the capture agent to a solid phase material before the performance of the assay or during the performance of the assay. The solid phase can, for example, be plastic, derivatized plastic, magnetic or non-magnetic metal, glass or silicon, including, for example, a test tube, microtiter well, sheet, bead, microparticle, chip, and other configurations known to those of ordinary skill in the art.

As used herein, term "microparticle" refers to a small particle that is recoverable by ultracentrifugation. Microparticles typically have an average diameter on the order of about 1 micron or less.

The term "capture agent" is used herein to refer to a binding partner that binds to analyte, preferably specifically. Capture agents can be attached to a solid phase. As used herein, the binding of a solid phase-affixed capture agent to analyte forms a "solid phase-affixed complex."

The term "labeled detection agent" is used herein to refer to a binding partner that binds to analyte, preferably specifically, and is labeled with a detectable label or becomes labeled with a detectable label during use in an assay.

A "detectable label" includes a moiety that is detectable or that can be rendered detectable.

As used with reference to a labeled detection agent, a "direct label" is a detectable label that is attached, by any means, to the detection agent.

As used with reference to a labeled detection agent, an "indirect label" is a detectable label that specifically binds the detection agent. Thus, an indirect label includes a moiety that is the specific binding partner of a moiety of the detection agent. Biotin and avidin are examples of such moieties that are employed, for example, by contacting a biotinylated antibody with labeled avidin to produce an indirectly labeled antibody.

As used herein, the term "indicator reagent" refers to any agent that is contacted with a label to produce a detectable signal. Thus, for example, in conventional enzyme labeling, an antibody labeled with an enzyme can be contacted with a substrate (the indicator reagent) to produce a detectable signal, such as a colored reaction product.

As used herein, an "antibody" refers to a protein consisting of one or more polypeptides substantially encoded by immunoglobulin genes or fragments of immunoglobulin genes. This term encompasses polyclonal antibodies, monoclonal antibodies, and fragments thereof, as well as molecules engineered from immunoglobulin gene sequences. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain (VL)" and "variable heavy chain (VH)" refer to these light and heavy chains respectively.

Antibodies exist as intact immunoglobulins or as a number of well-characterized fragments produced by digestion with various peptidases. Thus, for example, pepsin digests an antibody below the disulfide linkages in the hinge region to produce F(ab')2, a dimer of Fab which itself is a light chain joined to VH-CH1 by a disulfide bond. The F(ab')2 may be reduced under mild conditions to break the disulfide linkage in the hinge region thereby converting the (Fab')2 dimer into a Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology.

Thus, the term "antibody," as used herein also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (sFv or scFv), in which a variable heavy and a variable light chain are joined together (directly or through a peptide linker) to form a continuous polypeptide. The single chain Fv antibody is a covalently linked VH-VL heterodimer which may be expressed from a nucleic acid including VH- and VL-encoding sequences either joined directly or joined by a peptide-encoding linker. Huston, et al. (1988) Proc. Nat. Acad. Sci. USA, 85: 5879-5883. While the VH and VL are connected to each as a single polypeptide chain, the VH and VL domains associate non-covalently. The scFv antibodies and a number of other structures converting the naturally aggregated, but chemically separated, light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778).

An "autoantibody" is an antibody that binds to an analyte that is naturally occurring in the individual in which the antibody is produced. A "cardiac troponin-troponin-reactive autoantibody" is an autoantibody that binds cardiac troponin.

As used herein, a "species-specific antibody" refers to an antibody that specifically binds target antibodies from a particular species, regardless of the antigen-binding specificity of the target antibodies.

A "human-specific antibody" is an antibody that specifically binds human antibodies, e.g., human autoantibodies.

As used herein, a "cardiac troponin-reactive antibody or autoantibody" refers to an antibody or autoantibody, respectively that binds a cardiac troponin or fragment or complex thereof.

A "labeled cardiac troponin-reactive antibody" is a cardiac troponin-reactive antibody that is labeled with a detectable label or that becomes labeled with a detectable label during immunoassay.

Sample Collection and Processing

The assay methods of the invention are generally carried out on biological samples derived from an animal, preferably a mammal, and more preferably a human.

The methods of the invention can be carried out using any sample that may contain cardiac troponin-reactive autoantibodies. Convenient samples include, for example, blood, serum, and plasma.

The sample may be pretreated as necessary by dilution in an appropriate buffer solution or concentrated, if desired. Any of a number of standard aqueous buffer solutions, employing any of a variety of buffers, such as phosphate, Tris, or the like, optionally at physiological pH, can be used.

Assay of Cardiac Troponin-Reactive Autoantibodies in Conjunction with Cardiac Troponin In particular embodiments, the invention provides a method of assessing the reliability of a cardiac troponin assay result. The method entails assaying a biological sample for an autoantibody specific for a cardiac troponin, wherein the presence of an elevated level of cardiac troponin-reactive autoantibody indicates that the cardiac troponin assay result is not reliable.

In certain embodiments, a method of assessing risk of cardiac pathology entails: (a) assaying a biological sample for a cardiac troponin and (b) assaying a biological sample for an autoantibody specific for a cardiac troponin. The presence of an elevated level of cardiac troponin and/or an elevated level of cardiac troponin-reactive autoantibody indicates an elevated risk of cardiac pathology.

These methods can be carried out on samples from asymptomatic subjects or subjects with one or more symptoms of cardiac pathology. For example, the subject may have chest pain or some other indication of myocardial infarction.

The assay for cardiac troponin-reactive autoantibody can be carried out before, simultaneously with, in the absence of, or after the cardiac troponin assay. The assay for cardiac troponin-reactive antibody can be carried out using the same sample or a different sample from the same subject. If a different sample is used, it will generally be of the same type (e.g., blood) and taken at approximately the same time as the sample for the cardiac troponin assay.

Cardiac troponin-reactive autoantibodies can be detected and quantified by any of a number of methods well known to those of skill in the art. These may include any of a number of immunological methods such as fluid or gel precipitin reactions, immunodiffusion (single or double), affinity chromatography, immunoelectrophoresis, radioimmunoassay (RIA), enzyme-linked immunosorbent assays (ELISAs), immunofluorescent assays, Western blotting, and the like. Immunoassays useful in the methods of the invention are discussed in greater detail below.

The assays are scored in accordance with standard practice and may include the use of positive and/or negative controls and/or or standards containing known concentrations of cardiac troponin-reactive antibodies. The level of cardiac troponin-reactive autoantibodies is compared with a control level or control range, which can be determined when the assay is carried out or, more conveniently, can be predetermined. Any increase in the test sample relative to the control level or range can be assessed for significance by conventional statistical methods. The presence of an elevated level of cardiac troponin autoantibodies indicates that such antibodies may negatively interfere with the cardiac troponin measurement, rendering this value unreliable with respect to assessing the risk of cardiac pathologies, such as myocardial infarction.

In particular embodiments, when a subject is determined to have an elevated level of cardiac troponin-reactive autoantibodies, the subject is assessed for one or more additional indicators of cardiac pathology such as myoglobin, CK-MB, BNP, CRP, Troponin-I, Troponin-T, blood oxygen level, cardiac imaging, electrocardiography and the like.

A subject determined to have an elevated level of cardiac troponin-reactive autoantibodies may also be treated, e.g., for myocardial infarction in accordance with standard practice.

Methods of Diagnosing Cardiac Pathology

The invention also provides methods in which cardiac troponin-reactive antibodies are measured as indicators of the presence, or risk of, cardiac pathology.

Myocarditis, Cardiomyopathy, and Ischemic Heart Disease

In particular embodiments, the invention provides a method of screening for a subject having, or at risk of having, myocarditis, ischemic heart disease, or cardiomyopathy. In variations of these embodiments the cardiomyopathy is not dilated cardiomyopathy. Thus, for example, the method can be employed to screen for subjects having, or at risk of having hypertrophic cardiomyopathy and/or restrictive cardiomyopathy.

The method entails assaying a biological sample from the subject for an autoantibody specific for a cardiac troponin, wherein the presence of an elevated level of cardiac troponin-reactive autoantibody indicates the presence of, or risk of, cardiac pathology. This method can be performed in conjunction with one or more other tests, including but not limited to physical examination, and/or the taking of a medical history to allow a differential diagnosis of, e.g., myocarditis, ischemic heart disease, or hypertrophic or restrictive cardiomyopathy. The various tests and parameters employed in diagnosing these disorders are well known to those of skill in the art.

These methods can be carried out on samples from asymptomatic subjects or subjects having one or more risk factors associated with, or symptoms of, cardiac pathology. For example, the subject may have an autoimmune disease, high blood pressure, or may have close (e.g., first-degree) relative with a heritable cardiac pathology, such as hypertrophic cardiomyopathy.

Cardiac troponin-reactive autoantibodies can be detected and quantified by any convenient means. Examples of various immunoassay formats suitable for this purpose are described below. The assays are scored in accordance with standard practice.

In particular embodiments, when a subject is determined to have an elevated level of cardiac troponin-reactive autoantibodies, the subject is assessed for one or more additional indicators of cardiac pathology such as myoglobin, CK-MB, BNP, CRP, Troponin-I, Troponin-T, blood oxygen level, cardiac imaging, electrocardiography and the like.

Relatives of Individuals with Autoimmune Disease

The methods of the invention can be carried to identify cardiac pathology or risk thereof in subjects who have an autoimmune disease or who are related to an individual with an autoimmune disease. Subjects who are, e.g., first-degree or second-degree relatives of an individual with an autoimmune disease can be assessed using the methods of the invention.

The method entails assaying a biological sample from the subject for an autoantibody specific for a cardiac troponin, wherein the presence of an elevated level of cardiac troponin-reactive autoantibody indicates the presence of, or risk of, cardiac pathology. This method can be performed in conjunction with one or more other tests, physical examination, and/or the taking of a medical history to allow a differential diagnosis of, e.g., myocarditis, ischemic heart disease, or dilated, hypertrophic, or restrictive cardiomyopathy. The various tests and parameters employed in diagnosing these disorders are well known to those of skill in the art.

These methods can be carried out on samples from asymptomatic subjects or subjects having one or more risk factors associated with, or symptoms of, cardiac pathology.

Cardiac troponin-reactive autoantibodies can be detected and quantified by any convenient means. Examples of various immunoassay formats suitable for this purpose are described below. The assays are scored in accordance with standard practice.

In particular embodiments, when a subject is determined to have an elevated level of cardiac troponin-reactive autoantibodies, the subject is assessed for one or more additional indicators of cardiac pathology such as myoglobin, CK-MB, BNP, CRP, Troponin-I, Troponin-T, blood oxygen level, cardiac imaging, electrocardiography and the like.

Method of Identifying Candidates for Immunosuppressive or Immunoabsorption Therapies In particular embodiments, the invention provides a method of determining whether a subject having, or at risk for, a cardiac pathology is a candidate for immunosuppressive therapy or immunoabsorption therapy. Generally, the subject is one who has experienced some symptom of cardiac pathology or who has actually been diagnosed as having, or being at risk for, a cardiac pathology.

The method entails assaying a biological sample from the subject for an autoantibody specific for a cardiac troponin, wherein the presence of an elevated level of cardiac troponin-reactive autoantibody indicates that autoimmunity may be contributing to the subject's cardiac pathology or risk thereof. This method can be performed in conjunction with one or more other tests, physical examination, and/or the taking of a medical history in accordance with standard practice for diagnosing cardiac pathologies and/or autoimmune diseases.

Cardiac troponin-reactive autoantibodies can be detected and quantified by any convenient means, including any of those described herein. The assays are scored in accordance with standard practice.

A subject determined to have an elevated level of cardiac troponin-reactive autoantibodies may also be treated with immunosuppressive therapy or immunoabsorption therapy in accordance with standard practice.

Immunoassay Methods

In General

The immunoassay methods of the invention can be carried out in any of a wide variety of formats. For a general review of immunoassays, see Methods in Cell Biology Volume 37: Antibodies in Cell Biology, Asai, ed. Academic Press, Inc. New York (1993); Basic and Clinical Immunology 7th Edition, Stites & Ten, eds. (1991), which is incorporated by reference in its entirety.

In particular embodiments, an immunoassay method of the invention can be performed by contacting a biological sample with a cardiac troponin antigen, under conditions sufficient for binding of the cardiac troponin antigen to any cardiac troponin-reactive autoantibody present in the sample. Autoantibodies are detected/quantitated by detecting complex(es) comprising the cardiac troponin antigen bound to cardiac troponin-reactive autoantibody. Such assays can be homogeneous or heterogeneous (i.e., employing a solid phase). In heterogeneous assays, a capture agent that binds to the analyte (here, cardiac troponin-reactive autoantibodies) is typically affixed to a solid phase.

Cardiac troponin autoantibodies can be measured in a non-competitive immunoassay, wherein the amount of cardiac troponin antigen bound to cardiac troponin-reactive autoantibody is positively correlated with the concentration of cardiac troponin-reactive autoantibody present in the sample.

Thus, for example, the method can be carried out as an agglutination assay in which the biological sample is contacted with a cardiac troponin antigen affixed to a solid phase, such as a microparticle. The binding of cardiac troponin-reactive autoantibody present in the sample to the microparticles results in the agglutination of those microparticles, which can be detected, for example, by visual inspection of the sample. The microparticles can be colored or labeled, if desired, to facilitate detection of agglutination. The degree of agglutination is positively correlated with the concentration of cardiac troponin-reactive autoantibody present in the sample.

In other embodiments, the biological sample is contacted with a cardiac troponin antigen (which may, but need not, be affixed to a solid phase) and also contacted with a species-specific antibody, wherein the species-specific antibody is specific for the species from which the biological sample was obtained. Means for correcting interference generated by such autoantibodies is independently described in the patent application entitled "Immunoassay of Analytes in Samples Containing Endogenous Anti-Analyte Antibodies", Ser. No. 60/854,569, filed Oct. 26, 2006, as Express Mail Label No. EV 713761340 US, and is incorporated herein by reference in its entirety. This step is carried out under conditions sufficient for specific binding of the species-specific antibody to any cardiac troponin-reactive autoantibody present. Autoantibodies are detected/quantitated by detecting complex(es) comprising the cardiac troponin antigen bound to cardiac troponin-reactive autoantibody, which is bound to species-specific antibody. The sample may be contacted with the cardiac troponin antigen and the species-specific antibody simultaneously or sequentially, in any order. Regardless of the order of contact, if cardiac troponin-reactive autoantibodies are present in the sample, a complex forms that contains the antibodies "sandwiched" between the cardiac troponin antigen and the species-specific antibody.

For example, in one format of a sandwich immunoassay, an embodiment of the invention, the cardiac troponin antigen is affixed to a solid phase, binding of the cardiac troponin antigen to any cardiac troponin-reactive autoantibody present in the sample forms a solid phase-affixed complex, and detecting comprises detecting a signal from the solid phase-affixed complex. In particular embodiments of this format, the solid phase-affixed complex is detected using a species-specific antibody that is directly or indirectly labeled. The bound entities are separated, if necessary, from free labeled species-specific antibody, typically by washing, and the signal from the bound label is detected.

In another format of a sandwich immunoassay, an embodiment of the invention, the species-specific antibody is affixed to a solid phase, binding of the species-specific antibody to any cardiac troponin-reactive autoantibody present in the sample forms a solid phase-affixed complex, which is then detected. In certain embodiments, the solid phase-affixed complex is detected using a cardiac troponin antigen that is directly or indirectly labeled. The bound entities are separated, if necessary, from free labeled cardiac troponin antigen, typically by washing, and the signal from the bound label is detected.

Cardiac troponin autoantibodies can also be measured in competitive immunoassay, wherein the signal is negatively correlated with the concentration of cardiac troponin-reactive autoantibody present in the sample. In an example of a competitive format, the biological sample is contacted with a cardiac troponin antigen (which may, but need not, be affixed to a solid phase) and also contacted with a labeled (directly or indirectly) cardiac troponin-reactive antibody. This step is carried out under conditions sufficient for specific binding of the labeled cardiac troponin-reactive antibody to the cardiac troponin antigen. Autoantibodies in the sample that are specific for cardiac troponin can compete with the labeled cardiac troponin-reactive antibody for binding to the cardiac troponin antigen. Accordingly, the higher the level of cardiac troponin-reactive autoantibody, the lower the binding of labeled cardiac troponin-reactive antibody to the cardiac troponin antigen.

The sample may be contacted with the cardiac troponin antigen and the labeled cardiac troponin-reactive antibody simultaneously or sequentially, in any order.

Competitive immunoassays of this type can be conveniently carried out using a solid phase-affixed cardiac troponin antigen. In this case, binding of the cardiac troponin antigen to labeled cardiac troponin-reactive antibody or to any cardiac troponin-reactive autoantibody present in the sample forms a solid phase-affixed complex, and detection entails detecting a signal from the solid phase-affixed complex. The bound entities are separated, if necessary, from free labeled cardiac troponin-reactive antibody, typically by washing, and the signal from the bound label is detected.

Capture Agent

Capture agents useful in the immunoassay methods of the invention include those that bind cardiac troponin-reactive autoantibodies and can be affixed to a solid phase. Convenient capture agents include a cardiac troponin antigen and species-specific antibodies, wherein the species-specific antibody is specific for the species from which the biological sample was obtained. As those of skill in the art appreciate, cardiac troponin antigen represents a specific capture agent because it binds (captures) cardiac troponin-reactive autoantibodies. By contrast, species-specific antibodies represent a non-specific capture agent because such antibodies bind autoantibodies, regardless of specificity. In a sandwich immunoassay, a non-specific capture agent is typically employed with a labeled detection agent that specifically binds the analyte. Thus, for example, solid phase affixed species-specific antibodies can be used in conjunction with a labeled cardiac troponin antigen to specifically detect anti-cardiac troponin autoantibodies.

Cardiac Troponin Antigens

Cardiac troponin antigens useful in the immunoassay methods of the invention include cardiac troponin I, cardiac troponin T, cardiac troponin C, a fragment, derivative or complex thereof. Complexes useful in the invention can contain two different troponins (e.g., cTnI and cTnC) or all three.

In particular embodiments, the cardiac troponin antigen is a cardiac troponin amino acid sequence that can be derived from any cardiac troponin-like polypeptide from any organism. Cardiac troponin amino acid sequences useful in the invention are generally those derived from vertebrates, preferably from birds or mammals, more preferably from animals having research or commercial value or value as pets, such as mice, rats, guinea pigs, rabbits, cats, dogs, chickens, pigs, sheep, goats, cows, horses, as well as monkeys and other primates. In particular embodiments, the cardiac troponin amino acid sequence is derived from a human polypeptide.

The methods of the invention can employ full-length cardiac troponin antigens or one or more cardiac troponin fragments. Fragments will generally have at least one epitope to which an autoantibody can bind. Such fragments can have a length, e.g., of about 125, 100, 75, 50, 25, or 15 amino acids or a length that falls within a range with endpoints defined by any of these values (e.g., 15-125, 25-100, 50-75, 15-100, etc.). Those of skill in the art readily appreciate that the use of a cardiac troponin antigen having a larger number of natural epitopes (e.g., a full-length cardiac troponin) will generally provide a more comprehensive measurement of autoantibodies of different specificities than the use of a cardiac troponin antigen having a smaller number of natural epitopes. Accordingly, it is generally preferable to employ a cardiac troponin antigen that has a substantially native conformation or one or more peptides comprising troponin epitopes reactive with the autoantibody.

The cardiac troponin amino acid sequence can be a wild-type amino acid sequence or an amino acid sequence variant of the corresponding region of a wild-type polypeptide. In certain embodiments, cardiac troponin antigens include a wild-type cardiac troponin amino acid sequence or a cardiac troponin amino acid sequence containing conservative amino acid substitutions, as defined above.

In addition to the amino acid sequences described above, cardiac troponin antigens useful in the invention can include other amino acid sequences, including those from heterologous proteins. Accordingly, the invention encompasses fusion polypeptides in which a cardiac troponin amino acid sequence is fused, at either or both ends, to amino acid sequence(s) from one or more heterologous proteins. Examples of additional amino acid sequences often incorporated into proteins of interest include a signal sequence, which facilitates purification of the protein, and an epitope tag, which can be used for immunological detection or affinity purification.

Cardiac troponin polypeptides according to the invention can be synthesized using methods known in the art, such as for example exclusive solid phase synthesis, partial solid phase synthesis, fragment condensation, and classical solution synthesis. See, e.g., Merrifield, J. Am. Chem. Soc., 85:2149 (1963). For a description of solid phase peptide synthesis procedures, see John Morrow Stewart and Janis Dillaha Young, Solid Phase Peptide Syntheses (2nd Ed., Pierce Chemical Company, 1984).

Cardiac troponin polypeptides can also produced using recombinant techniques. In certain embodiments, the sequence of a cardiac troponin coding region is used as a guide to design a synthetic nucleic acid molecule encoding the cardiac troponin polypeptide that can be incorporated an expression vector. Methods for constructing synthetic genes are well-known to those of skill in the art. See, e.g., Dennis, M. S., Carter, P. and Lazarus, R. A. (1993) Proteins: Struct. Funct. Genet., 15:312-321.

The expression vector includes one or more control sequences capable of effecting and/or enhancing the expression of an operably linked polypeptide coding sequence. Control sequences that are suitable for expression in prokaryotes, for example, include a promoter sequence, an operator sequence, and a ribosome binding site. Control sequences for expression in eukaryotic cells include a promoter, an enhancer, and a transcription termination sequence (i.e., a polyadenylation signal).

An expression vector according to the invention can also include other sequences, such as, for example, nucleic acid sequences encoding a signal sequence or an amplifiable gene. A signal sequence can direct the secretion of a polypeptide fused thereto from a cell expressing the protein. In the expression vector, nucleic acid encoding a signal sequence is linked to a polypeptide coding sequence so as to preserve the reading frame of the polypeptide coding sequence. The inclusion in a vector of a gene complementing an auxotrophic deficiency in the chosen host cell allows for the selection of host cells transformed with the vector.

A wide variety of host cells are available for propagation and/or expression of vectors. Examples include prokaryotic cells (such as E. coli and strains of Bacillus, Pseudomonas, and other bacteria), yeast or other fungal cells (including S. cerevesiae and P. pastoris), insect cells, plant cells, and phage, as well as higher eukaryotic cells (such as human embryonic kidney cells and other mammalian cells).

Vectors expressing cardiac troponin can be introduced into a host cell by any convenient method, which will vary depending on the vector-host system employed. Generally, a vector is introduced into a host cell by transformation (also known as "transfection") or infection with a virus (e.g., phage) bearing the vector. If the host cell is a prokaryotic cell (or other cell having a cell wall), convenient transformation methods include the calcium treatment method described by Cohen, et al. (1972) Proc. Natl. Acad. Sci., USA, 69:2110-14. If a prokaryotic cell is used as the host and the vector is a phagemid vector, the vector can be introduced into the host cell by infection. Yeast cells can be transformed using polyethylene glycol, for example, as taught by Hinnen (1978) Proc. Natl. Acad. Sci, USA, 75:1929-33. Mammalian cells are conveniently transformed using the calcium phosphate precipitation method described by Graham, et al. (1978) Virology, 52:546 and by Gorman, et al. (1990) DNA and Prot. Eng. Tech., 2:3-10. However, other known methods for introducing DNA into host cells, such as nuclear injection, electroporation, and protoplast fusion also are acceptable for use in the invention.

Expression of cardiac troponin from a transformed host cell entails culturing the host cell under conditions suitable for cell growth and expression and recovering the expressed polypeptides from a cell lysate or, if the polypeptides are secreted, from the culture medium. In particular, the culture medium contains appropriate nutrients and growth factors for the host cell employed. The nutrients and growth factors are, in many cases, well known or can be readily determined empirically by those skilled in the art. Suitable culture conditions for mammalian host cells, for instance, are described in Mammalian Cell Culture (Mather ed., Plenum Press 1984) and in Barnes and Sato (1980) Cell 22:649.

In addition, the culture conditions should allow transcription, translation, and protein transport between cellular compartments. Factors that affect these processes are well-known and include, for example, DNA/RNA copy number; factors that stabilize DNA; nutrients, supplements, and transcriptional inducers or repressors present in the culture medium; temperature, pH and osmolality of the culture; and cell density. The adjustment of these factors to promote expression in a particular vector-host cell system is within the level of skill in the art. Principles and practical techniques for maximizing the productivity of in vitro mammalian cell cultures, for example, can be found in Mammalian Cell Biotechnology: a Practical Approach (Butler ed., IRL Press (1991).

Any of a number of well-known techniques for large- or small-scale production of proteins can be employed in expressing the polypeptides of the invention. These include, but are not limited to, the use of a shaken flask, a fluidized bed bioreactor, a roller bottle culture system, and a stirred tank bioreactor system. Cell culture can be carried out in a batch, fed-batch, or continuous mode.

Methods for recovery of recombinant proteins produced as described above are well-known and vary depending on the expression system employed. A polypeptide including a signal sequence can be recovered from the culture medium or the periplasm. Polypeptides can also be expressed intracellularly and recovered from cell lysates.

The expressed polypeptides can be purified from culture medium or a cell lysate by any method capable of separating the polypeptide from one or more components of the host cell or culture medium. Typically, the polypeptide is separated from host cell and/or culture medium components that would interfere with the intended use of the polypeptide. As a first step, the culture medium or cell lysate is usually centrifuged or filtered to remove cellular debris. The supernatant is then typically concentrated or diluted to a desired volume or diafiltered into a suitable buffer to condition the preparation for further purification.

The polypeptide can then be further purified using well-known techniques. The technique chosen will vary depending on the properties of the expressed polypeptide. If, for example, the polypeptide is expressed as a fusion protein containing an epitope tag or other affinity domain, purification typically includes the use of an affinity column containing the cognate binding partner. For instance, polypeptides fused with green fluorescent protein, hemagglutinin, or FLAG epitope tags or with hexahistidine or similar metal affinity tags can be purified by fractionation on an affinity column.

Antibodies

Antibodies useful in the immunoassay methods of the invention include polyclonal and monoclonal antibodies. Polyclonal antibodies are raised by injecting (e.g., subcutaneous or intramuscular injection) an immunogen into a suitable non-human mammal (e.g., a mouse or a rabbit). Generally, the immunogen should induce production of high titers of antibody with relatively high affinity for the target antigen.

If desired, the antigen may be conjugated to a carrier protein by conjugation techniques that are well known in the art. Commonly used carriers include keyhole limpet hemocyanin (KLH), thyroglobulin, bovine serum albumin (BSA), and tetanus toxoid. The conjugate is then used to immunize the animal.

The antibodies are then obtained from blood samples taken from the animal. The techniques used to produce polyclonal antibodies are extensively described in the literature (see, e.g., Methods of Enzymology, "Production of Antisera With Small Doses of Immunogen: Multiple Intradermal Injections," Langone, et al. eds. (Acad. Press, 1981)). Polyclonal antibodies produced by the animals can be further purified, for example, by binding to and elution from a matrix to which the target antigen is bound. Those of skill in the art will know of various techniques common in the immunology arts for purification and/or concentration of polyclonal, as well as monoclonal, antibodies see, for example, Coligan, et al. (1991) Unit 9, Current Protocols in Immunology, Wiley Interscience.

For many applications, monoclonal antibodies (mAbs) are preferred. The general method used for production of hybridomas secreting mAbs is well known (Kohler and Milstein (1975) Nature, 256:495). Briefly, as described by Kohler and Milstein, the technique entailed isolating lymphocytes from regional draining lymph nodes of five separate cancer patients with either melanoma, teratocarcinoma or cancer of the cervix, glioma or lung, (where samples were obtained from surgical specimens), pooling the cells, and fusing the cells with SHFP-1. Hybridomas were screened for production of antibody that bound to cancer cell lines. Confirmation of specificity among mAbs can be accomplished using routine screening techniques (such as the enzyme-linked immunosorbent assay, or "ELISA") to determine the elementary reaction pattern of the mAb of interest.

As used herein, the term "antibody" encompasses antigen-binding antibody fragments, e.g., single chain antibodies (scFv or others), which can be produced/selected using phage display technology. The ability to express antibody fragments on the surface of viruses that infect bacteria (bacteriophage or phage) makes it possible to isolate a single binding antibody fragment, e.g., from a library of greater than $10^{10}$ nonbinding clones. To express antibody fragments on the surface of phage (phage display), an antibody fragment gene is inserted into the gene encoding a phage surface protein (e.g., pIII) and the antibody fragment-pIII fusion protein is displayed on the phage surface (McCafferty et al. (1990) Nature, 348: 552-554; Hoogenboom et al. (1991) Nucleic Acids Res. 19: 4133-4137).

Since the antibody fragments on the surface of the phage are functional, phage-bearing antigen-binding antibody fragments can be separated from non-binding phage by antigen affinity chromatography (McCafferty et al. (1990) Nature, 348: 552-554). Depending on the affinity of the antibody fragment, enrichment factors of 20-fold-1,000,000-fold are obtained for a single round of affinity selection. By infecting bacteria with the eluted phage, however, more phage can be grown and subjected to another round of selection. In this way, an enrichment of 1000-fold in one round can become 1,000,000-fold in two rounds of selection (McCafferty et al. (1990) Nature, 348: 552-554). Thus, even when enrichments are low (Marks et al. (1991) J. Mol. Biol. 222: 581-597), multiple rounds of affinity selection can lead to the isolation of rare phage. Since selection of the phage antibody library on antigen results in enrichment, the majority of clones bind antigen after as few as three to four rounds of selection. Thus only a relatively small number of clones (several hundred) need to be analyzed for binding to antigen.

Human antibodies can be produced without prior immunization by displaying very large and diverse V-gene repertoires on phage (Marks et al. (1991) J. Mol. Biol. 222: 581-597). In one embodiment, natural VH and VL repertoires present in human peripheral blood lymphocytes are isolated from unimmunized donors by PCR. The V-gene repertoires can be spliced together at random using PCR to create a scFv gene repertoire which can be cloned into a phage vector to create a library of 30 million phage antibodies (Id.). From a single "naïve" phage antibody library, binding antibody fragments have been isolated against more than 17 different antigens, including haptens, polysaccharides, and proteins (Marks et al. (1991) J. Mol. Biol. 222: 581-597; Marks et al. (1993). Bio/Technology. 10: 779-783; Griffiths et al. (1993) EMBO J. 12: 725-734; Clackson et al. (1991) Nature. 352: 624-628). Antibodies have been produced against self proteins, including human thyroglobulin, immunoglobulin, tumor necrosis factor, and CEA (Griffiths et al. (1993) EMBO J. 12: 725-734). The antibody fragments are highly specific for the antigen used for selection and have affinities in the 1 nM to 100 nM range (Marks et al. (1991) J. Mol. Biol. 222: 581-597; Griffiths et al. (1993) EMBO J. 12: 725-734). Larger phage antibody libraries result in the isolation of more antibodies of higher binding affinity to a greater proportion of antigens.

As those of skill in the art readily appreciate, antibodies can be prepared by any of a number of commercial services (e.g., Berkeley Antibody Laboratories, Bethyl Laboratories, Anawa, Eurogenetec, etc.).

Solid Phase

For embodiments of the invention that employ a solid phase as a support for the capture agent, the solid phase can be any suitable material with sufficient surface affinity to bind a capture agent. Useful solid supports include: natural polymeric carbohydrates and their synthetically modified, crosslinked, or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer. All of these materials may be used in suitable shapes, such as films, sheets, tubes, particulates, or plates, or they may be coated onto, bonded, or laminated to appropriate inert carriers, such as paper, glass, plastic films, fabrics, or the like.

Nitrocellulose has excellent absorption and adsorption qualities for a wide variety of reagents including monoclonal antibodies. Nylon also possesses similar characteristics and also is suitable.

Preferred solid phase materials for flow-through assay devices include filter paper such as a porous fiberglass material or other fiber matrix materials. The thickness of such material is not critical and will be a matter of choice, largely based upon the properties of the sample or analyte being assayed, such as the fluidity of the biological sample.

Alternatively, the solid phase can constitute microparticles. Microparticles useful in the invention can be selected by one skilled in the art from any suitable type of particulate material and include those composed of polystyrene, polymethylacrylate, polypropylene, latex, polytetrafluoroethylene, polyacrylonitrile, polycarbonate, or similar materials. Further, the microparticles can be magnetic or paramagnetic microparticles, so as to facilitate manipulation of the microparticle within a magnetic field.

Microparticles can be suspended in the mixture of soluble reagents and biological sample or can be retained and immobilized by a support material. In the latter case, the microparticles on or in the support material are not capable of substantial movement to positions elsewhere within the support material. Alternatively, the microparticles can be separated from suspension in the mixture of soluble reagents and biological sample by sedimentation or centrifugation. When the microparticles are magnetic or paramagnetic the microparticles can be separated from suspension in the mixture of soluble reagents and biological sample by a magnetic field.

The methods of the present invention can be adapted for use in systems that utilize microparticle technology including automated and semi-automated systems wherein the solid phase comprises a microparticle. Such systems include those described in pending U.S. App. No. 425,651 and U.S. Pat. No. 5,089,424, which correspond to published EPO App. Nos. EP 0 425 633 and EP 0 424 634, respectively, and U.S. Pat. No. 5,006,309.

In particular embodiments, the solid phase includes one or more electrodes. Capture agent(s) can be affixed, directly or indirectly, to the electrode(s). In one embodiment, for example, capture agents can be affixed to magnetic or paramagnetic microparticles, which are then positioned in the vicinity of the electrode surface using a magnet. Systems in which one or more electrodes serve as the solid phase are useful where detection is based on electrochemical interactions. Exemplary systems of this type are described, for example, in U.S. Pat. No. 6,887,714 (issued May 3, 2005). The basic method is described further below with respect to electrochemical detection.

The capture agent can be attached to the solid phase by adsorption, where it is retained by hydrophobic forces. Alternatively, the surface of the solid phase can be activated by chemical processes that cause covalent linkage of the capture agent to the support.

To change or enhance the intrinsic charge of the solid phase, a charged substance can be coated directly onto the solid phase. Ion capture procedures for immobilizing an immobilizable reaction complex with a negatively charged polymer, described in U.S. App. No. 150,278, corresponding to EP Publication No. 0326100, and U.S. App. No. 375,029 (EP Publication No. 0406473), can be employed according to the present invention to affect a fast solution-phase immunochemical reaction. In these procedures, an immobilizable immune complex is separated from the rest of the reaction mixture by ionic interactions between the negatively charged polyanion/immune complex and the previously treated, positively charged matrix and detected by using any of a number of signal-generating systems, including, e.g., chemiluminescent systems, as described in U.S. App. No. 921,979, corresponding to EPO Publication No. 0 273,115.

If the solid phase is silicon or glass, the surface must generally be activated prior to attaching the specific binding partner. Activated silane compounds such as triethoxy amino propyl silane (available from Sigma Chemical Co., St. Louis, Mo.), triethoxy vinyl silane (Aldrich Chemical Co., Milwaukee, Wis.), and (3-mercapto-propyl)-trimethoxy silane (Sigma Chemical Co., St. Louis, Mo.) can be used to introduce reactive groups such as amino-, vinyl, and thiol, respectively. Such activated surfaces can be used to link the capture directly (in the cases of amino or thiol), or the activated surface can be further reacted with linkers such as glutaraldehyde, bis(succinimidyl)suberate, SPPD 9 succinimidyl 3-[2-pyridyldithio]propionate), SMCC (succinimidyl-4-[Nmaleimidomethyl]cyclohexane-1-carboxylate), SLAB (succinimidyl [4iodoacetyl]aminobenzoate), and SMPB (succinimidyl 4-[1maleimidophenyl]butyrate) to separate the capture agent from the surface. Vinyl groups can be oxidized to provide a means for covalent attachment. Vinyl groups can also be used as an anchor for the polymerization of various polymers such as poly-acrylic acid, which can provide multiple attachment points for specific capture agents. Amino groups can be reacted with oxidized dextrans of various molecular weights to provide hydrophilic linkers of different size and capacity. Examples of oxidizable dextrans include Dextran T-40 (molecular weight 40,000 daltons), Dextran T-110 (molecular weight 110,000 daltons), Dextran T-500 (molecular weight 500,000 daltons), Dextran T-2M (molecular weight 2,000,000 daltons) (all of which are available from Pharmacia, Piscataway, N.J.), or Ficoll (molecular weight 70,000 daltons; available from Sigma Chemical Co., St. Louis, Mo.). Additionally, polyelectrolyte interactions can be used to immobilize a specific capture agent on a solid phase using techniques and chemistries described U.S. App. No. 150,278, filed Jan. 29, 1988, and U.S. App. No. 375,029, filed Jul. 7, 1989, each of which is incorporated herein by reference.

Other considerations affecting the choice of solid phase include the ability to minimize non-specific binding of labeled entities and compatibility with the labeling system employed. For, example, solid phases used with fluorescent labels should have sufficiently low background fluorescence to allow signal detection.

Following attachment of a specific capture agent, the surface of the solid support may be further treated with materials such as serum, proteins, or other blocking agents to minimize non-specific binding.

Labeling Systems

As discussed above, many immunoassays according to the invention employ a labeled detection agent, such a labeled species-specific antibody and a labeled cardiac troponin antigen.

Detectable labels suitable for use in the detection agents of the present invention include any composition detectable by spectroscopic, photochemical, biochemical, immunochemical, electrical, optical, or chemical means. Useful labels in the present invention include magnetic beads (e.g., Dynabeads™), fluorescent dyes (e.g., fluorescein, Texas Red, rhodamine, green fluorescent protein, and the like, see, e.g., Molecular Probes, Eugene, Oreg., USA), chemiluminescent compounds such as acridinium (e.g., acridinium-9-carboxamide), phenanthridinium, dioxetanes, luminol and the like, radiolabels (e.g., $^3H$, $^{125}I$, $^{35}S$, $^{14}C$, or $^{32}P$), catalysts such as enzymes (e.g., horse radish peroxidase, alkaline phosphatase, beta-galactosidase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

The label can be attached to the detection agent prior to, or during, or after contact with the biological sample. So-called "direct labels" are detectable labels that are directly attached to or incorporated into detection agents prior to use in the assay. Direct labels can be attached to or incorporated into detection agents by any of a number of means well known to those of skill in the art.

In contrast, so-called "indirect labels" typically bind to the detection agent at some point during the assay. Often, the indirect label binds to a moiety that is attached to or incorporated into the detection agent prior to use. Thus, for example, an antibody used as a detection agent (a "detection antibody") can be biotinylated before use in an assay. During the assay, an avidin-conjugated fluorophore can bind the biotin-bearing detection agent, to provide a label that is easily detected.

In another example of indirect labeling, polypeptides capable of specifically binding immunoglobulin constant regions, such as polypeptide A or polypeptide G, can also be used as labels for detection antibodies. These polypeptides are normal constituents of the cell walls of streptococcal bacteria. They exhibit a strong non-immunogenic reactivity with immunoglobulin constant regions from a variety of species (see, generally Kronval, et al. (1973) J. Immunol., 111: 1401-1406, and Akerstrom (1985) J. Immunol., 135: 2589-2542). Such polypeptides can thus be labeled and added to the assay mixture, where they will bind to the detection antibody, as well as to the species-specific antibody, labeling both and providing a composite signal attributable to analyte and autoantibody present in the sample.

Some labels useful in the invention may require the use of an indicator reagent to produce a detectable signal. In an ELISA, for example, an enzyme label (e.g., beta-galactosidase) will require the addition of a substrate (e.g., X-gal) to produce a detectable signal.

Exemplary Formats

Fluorescence Polarization Immunoassay (FPIA)

In an exemplary embodiment, a fluorescent label is employed in a fluorescence polarization immunoassay (FPIA) according to the invention. Generally, fluorescent polarization techniques are based on the principle that a fluorescent label, when excited by plane-polarized light of a characteristic wavelength, will emit light at another characteristic wavelength (i.e., fluorescence) that retains a degree of the polarization relative to the incident light that is inversely related to the rate of rotation of the label in a given medium. As a consequence of this property, a label with constrained rotation, such as one bound to another solution component with a relatively lower rate of rotation, will retain a relatively greater degree of polarization of emitted light than when free in solution.

This technique can be employed in immunoassays according to the invention, for example, by selecting reagents such that binding of the fluorescently labeled entities forms a complex sufficiently different in size such that a change in the intensity light emitted in a given plane can be detected. For example, when a labeled cardiac troponin antigen is bound by one or more autoantibodies, the resulting complex is sufficiently larger, and its rotation is sufficiently constrained, relative to the free labeled cardiac troponin antigen that binding is easily detected.

Fluorophores useful in FPIA include fluorescein, aminofluorescein, carboxyfluorescein, and the like, preferably 5 and 6-aminomethylfluorescein, 5 and 6-aminofluorescein, 6-carboxyfluorescein, 5-carboxyfluorescein, thioureafluorescein, and methoxytriazinolyl-aminofluorescein, and similar fluorescent derivatives. Examples of commercially available automated instruments with which fluorescence polarization assays can be conducted include: the IMx system, the TDx system, and TDxFLx system (all available from Abbott Laboratories, Abbott Park, Ill.).

Scanning Probe Microscopy (SPM)

The use of scanning probe microscopy (SPM) for immunoassays also is a technology to which the immunoassay methods of the present invention are easily adaptable. In SPM, in particular in atomic force microscopy, the capture agent is affixed to a solid phase having a surface suitable for scanning. The capture agent can, for example, be adsorbed to a plastic or metal surface. Alternatively, the capture agent can be covalently attached to, e.g., derivatized plastic, metal, silicon, or glass according to methods known to those of ordinary skill in the art. Following attachment of the capture agent, the biological sample is contacted with the solid phase, and a scanning probe microscope is used to detect and quantify solid phase-affixed complexes. The use of SPM eliminates the need for labels which are typically employed in immunoassay systems. Such a system is described in U.S. App. No. 662,147, which is incorporated herein by reference.

MicroElectroMechanical Systems (MEMS)

Immunoassays according to the invention can also be carried out using a MicroElectroMechanical System (MEMS). MEMS are microscopic structures integrated onto silicon that combine mechanical, optical, and fluidic elements with electronics, allowing convenient detection of an analyte of interest. An exemplary MEMS device suitable for use in the invention is the Protiveris' multicantilever array. This array is based on chemo-mechanical actuation of specially designed silicon microcantilevers and subsequent optical detection of the microcantilever deflections. When coated on one side with a binding partner, a microcantilever will bend when it is exposed to a solution containing the complementary molecule. This bending is caused by the change in the surface energy due to the binding event. Optical detection of the degree of bending (deflection) allows measurement of the amount of complementary molecule bound to the microcantilever.

Electrochemical De Systems

In other embodiments, immunoassays according to the invention are carried out using electrochemical detection. A basic procedure for electrochemical detection has been described by Heineman and coworkers. This entailed immobilization of a primary antibody (Ab, rat-anti mouse IgG), followed by exposure to a sequence of solutions containing the antigen (Ag, mouse IgG), the secondary antibody conjugated to an enzyme label (AP-Ab, rat anti mouse IgG and alkaline phosphatase), and p-aminophenyl phosphate (PAPP). The AP converts PAPP to p-aminophenol ($PAP_R$, the "R" is intended to distinguish the reduced form from the oxidized form, $PAP_O$, the quinoneimine), which is electrochemically reversible at potentials that do not interfere with reduction of oxygen and water at pH 9.0, where AP exhibits optimum activity. $PAP_R$ does not cause electrode fouling, unlike phenol whose precursor, phenylphosphate, is often used as the enzyme substrate. Although $PAP_R$ undergoes air and light oxidation, these are easily prevented on small scales and short time frames. Picomole detection limits for $PAP_R$ and femtogram detection limits for IgG achieved in microelectrochemical immunoassays using PAPP volumes ranging from 20 mu.1 to 360 µL have been reported previously. In capillary immunoassays with electrochemical detection, the lowest detection limit reported thus far is 3000 molecules of mouse IgG using a volume of 70 µL and a 30 min or 25 min assay time.

In an exemplary embodiment employing electrochemical detection, a capture agent according to the invention can be immobilized on the surface of an electrode (the "solid phase"). The electrode is then contacted with a biological sample from, e.g., a human. Any anti-cardiac troponin antibodies in the sample bind to the capture agent to form a solid phase-affixed complex. Anti-human antibody, which is labeled with AP, for example, binds to autoantibodies in the complex, thereby becoming immobilized on the surface of the electrode. The addition of PAPP, results in its conversion by AP to $PAP_R$, which is then detected.

Various electrochemical detection systems are described in U.S. Pat. Nos. 7,045,364 (issued May 16, 2006; incorporated herein by reference), 7,045,310 (issued May 16, 2006; incorporated herein by reference), 6,887,714 (issued May 3, 2005; incorporated herein by reference), 6,682,648 (issued Jan. 27, 2004; incorporated herein by reference); 6,670,115 (issued Dec. 30, 2003; incorporated herein by reference).

The present invention is for example applicable to the jointly owned commercial Abbott Point of Care (i-STAT™) electrochemical immunoassay system which performs sandwich immunoassays for several cardiac markers, including TnI, CKMB and BNP. Immunosensors and ways of operating them in single-use test devices are described in jointly owned Publication Nos. US 20030170881, US 20040018577, US 20050054078, and US 20060160164, each of which is incorporated herein by reference. Additional background on the manufacture of electrochemical and other types of immunosensors is found in jointly owned U.S. Pat. No. 5,063,081 which is also incorporated by reference.

Multiplex Formats

In particular embodiments, useful, for example, for simultaneously assaying multiple analytes in one biological sample, the solid phase can include a plurality different capture agents, including one that captures troponin-reactive autoantibodies. Thus, for example, the solid phase can have affixed thereon a plurality of antigens, wherein each is intended to test for the presence of different autoantibodies in the sample. In an exemplary embodiment, the solid phase can consist of a plurality of different regions on a surface, wherein each region has a particular antigen affixed therein.

Multiplex formats can, but need not, employ a plurality of labels, wherein each label is used for the detection of autoantibodies reactive with a particular antigen. For example, multiple, different autoantibodies can be detected without using a plurality of labels where a plurality of capture agents, such as antigens, are affixed to the solid phase at different known locations, based on specificity. Because the specificity of the capture agent at each location is known, the detection of a signal at a particular location can be associated with the presence of autoantibodies bound at that location. Examples of this format include microfluidic devices and capillary arrays, containing different capture agents at different locations along a channel or capillary, respectively, and microarrays, which typically contain different capture agents arranged in a matrix of spots ("target elements") on a surface of a solid support. In particular embodiments, each different capture agent can be affixed to a different electrode, which can, for example, be formed on a surface of a solid support, in a channel of a microfluidic device, or in a capillary.

Test Kits

The invention also provides test kits for assaying biological samples for cardiac troponin autoantibodies. Test kits according to the invention include one or more reagents useful for practicing one or more immunoassays according to the invention. A test kit generally includes a package with one or more containers holding the reagents, as one or more separate compositions or, optionally, as admixture where the compatibility of the reagents will allow. The test kit can also include other material(s), which may be desirable from a user standpoint, such as a buffer(s), a diluent(s), a standard(s), and/or any other material useful in sample processing, washing, or conducting any other step of the assay.

In certain embodiments, a test kit includes a humanized monoclonal antibody, wherein the humanized monoclonal antibody is specific for a cardiac troponin. This component can be used as a positive control in immunoassays according to the invention. If desired, this component can be included in the test kit in multiple concentrations to facilitate the generation of a standard curve to which the signal detected in the test sample can be compared. Alternatively, a standard curve can be generated by preparing dilutions of a single humanized monoclonal antibody solution provided in the kit.

Kits according to the invention can include a solid phase and a capture agent affixed to the solid phase, wherein the capture agent is selected from the group consisting of a cardiac troponin antigen and a species-specific antibody, wherein the species-specific antibody is specific for the species from which the biological sample is to be obtained. Where such kits are to be employed for conducting sandwich immunoassays, the kits can additionally include a labeled detection agent. In such embodiments, if the capture agent is a cardiac troponin antigen, the detection agent can be a species-specific antibody. If the capture agent is a species-specific antibody, a cardiac troponin antigen can be used as the detection agent. In particular embodiments, the species-specific antibody is a human-specific antibody.

Test kits according to the invention can also include a labeled non-human monoclonal antibody that is specific for a cardiac troponin. This component is useful as a control for confirming that any cardiac troponin antigen employed is capable of binding antibody.

In certain embodiments, the test kit includes at least one direct label, such as acridinium-9-carboxamide. Test kits according to the invention can also include at least one indirect label. If the label employed generally requires an indicator reagent to produce a detectable signal, the test kit preferably includes one or more suitable indicator reagents.

In exemplary embodiments, the solid phase includes one or more microparticles or electrodes. Test kits designed for multiplex assays conveniently contain one or more solid phases including a plurality of antigens that are specific for a plurality of different autoantibodies. Thus, for example, a test kit designed for multiplex electrochemical immunoassays can contain a solid phase including a plurality of electrodes, with each electrode bearing a different antigen.

Test kits according to the invention preferably include instructions for carrying out one or more of the immunoassays of the invention. Instructions included in kits of the invention can be affixed to packaging material or can be included as a package insert. While the instructions are typically written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

EXAMPLES

The invention will be better understood through examples illustrating its use and efficacy. The following examples are offered to illustrate, but not to limit, the claimed invention.

Example 1

Cardiac Troponin-I-C Complex Microplate Preparation and Testing

Microplate Coating Procedure

The microplate coating solution was prepared by dissolving human cardiac troponin-I-C complex (cTnIC, commercial vendor) in phosphate buffer (0.2 M, pH 8) to give solutions at the following concentrations: 80, 400, 2000, or 10000 ng/mL. The coating solution (100 μL) was added to the wells of a white high-binding flat-bottom 96-well polystyrene microplate. The microplate was then sealed, placed on an orbital shaker at 28 rpm and incubated at 38° C. for 1 hour (h). The coating solution was then replaced with a blocking solution (300 μL) consisting of 2% wt/v bovine serum albumin (BSA) in phosphate buffered saline (PBS, pH 7.2) which was replaced with fresh blocking solution before the plate was sealed, placed on an orbital shaker at 28 rpm and incubated at 38° C. for 1 h. The coating solution was then replaced with an overcoating solution (300 μL) consisting of 2% wt/v sucrose in phosphate buffered saline (PBS, pH 7.2) which was replaced twice with fresh overcoating solution before the plate was sealed, placed on an orbital shaker at 28 rpm and incubated at 38° C. for 20 min. The overcoating solution was then removed and the microplate was dried at ambient temperature under a stream of dry nitrogen before storing desiccated at ambient temperature.

Activity of cTnIC-Coated Microplate

The immunoreactive response of the cTnIC-coated microplate was tested using reagents from the ARCHITECT® STAT-troponin I kit (Abbott Laboratories, Abbott Park, Ill.). The ARCHITECT® STAT-troponin I conjugate [Anti-cardiac troponin-I (mouse, monoclonal) acridinium labeled conjugate in MES buffer with protein (bovine) stabilizer. Preservative: ProClin® 300.] (100 μL) was added to the wells of the cTnIC-coated microplate. The microplate was then sealed, placed on an orbital shaker at 28 rpm and incubated at 38° C. for 1 h. The conjugate solution was then removed and the wells of the microplate were washed with the ARCHITECT® Line Diluent (3×300 μL).

Figure 2:
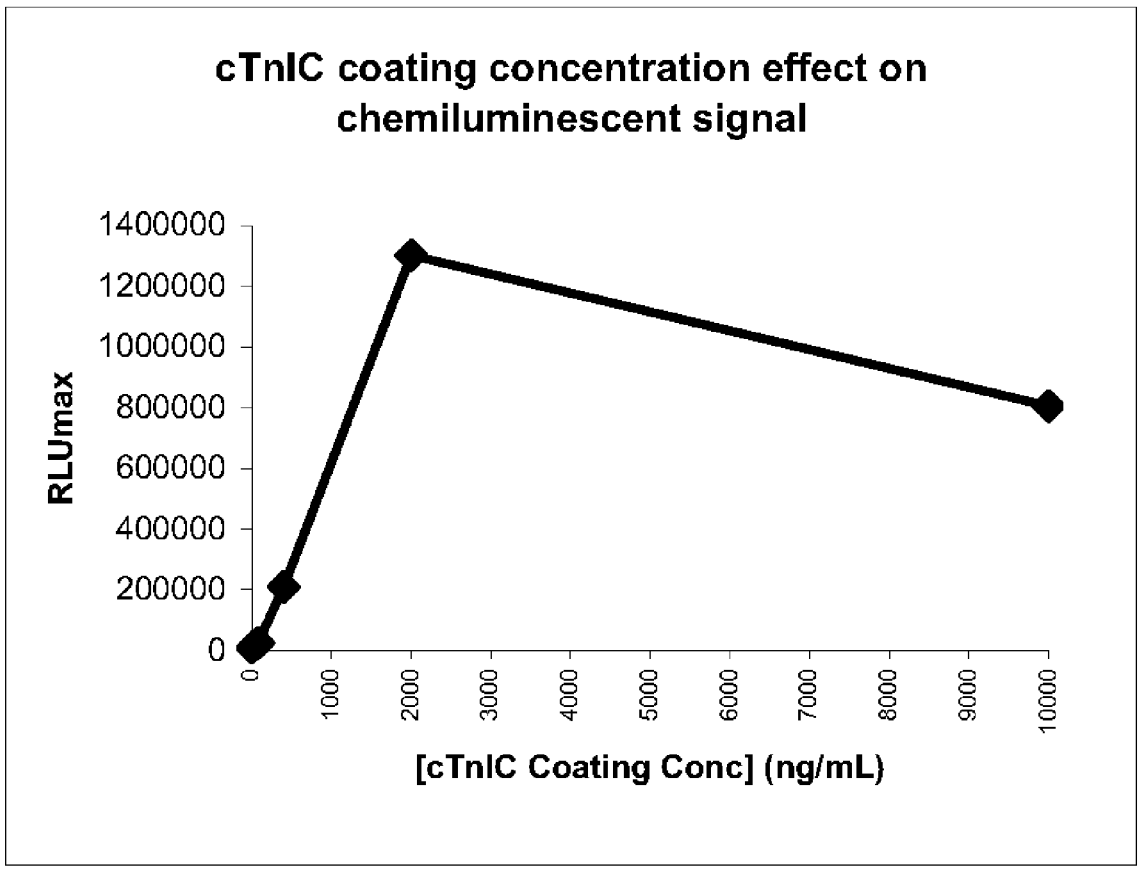
FIG. 2 is a graph showing cTnIC coating concentration effect on chemiluminescent signal as described in Example 1.

The formation of the anti-cardiac troponin-I acridinium-labeled mouse monoclonal antibody-cTnIC immunocomplex was measured on a Berthold Mithras microplate reader (Berthold Technologies Inc, Oak Ridge, Tenn.). The microplate was loaded into the instrument that had been equilibrated at 37° C. The ARCHITECT® Pre-Trigger solution (100 μL) was dispensed to each well. After the pre-trigger solution was added, the plate was shaken for 72 sec (s). Then the ARCHITECT® Trigger solution (100 μL) was dispensed to each well and chemiluminescent signal recorded for 2 s. The chemiluminescence signal (RLU, relative light units) was plotted against time (seconds) for each cTnIC coating concentration. The results are shown in FIGS. 1 and 2 and in Table 1. The maximum light output (RLUmax) and signal to noise (S/N) was observed at a coating concentration of 2000 ng/mL.

TABLE 1 cTnIC coating concentration effect on chemiluminescent signal

| Coating Solution (ng/mL) | Chemiluminescent Signal (RLUmax) | % CV | S/N |
|---|---|---|---|
| 0 | 10160 | 2.7 | 1 |
| 80 | 23350 | 8.8 | 3 |
| 400 | 182360 | 10.0 | 21 |
| 2000 | 1309770 | 1.8 | 133 |
| 10000 | 910150 | 8.6 | 82 |

Example 2

Analysis of Normal Donor Human Plasma for cTnIC Reactive Autoantibodies

Figure 3:
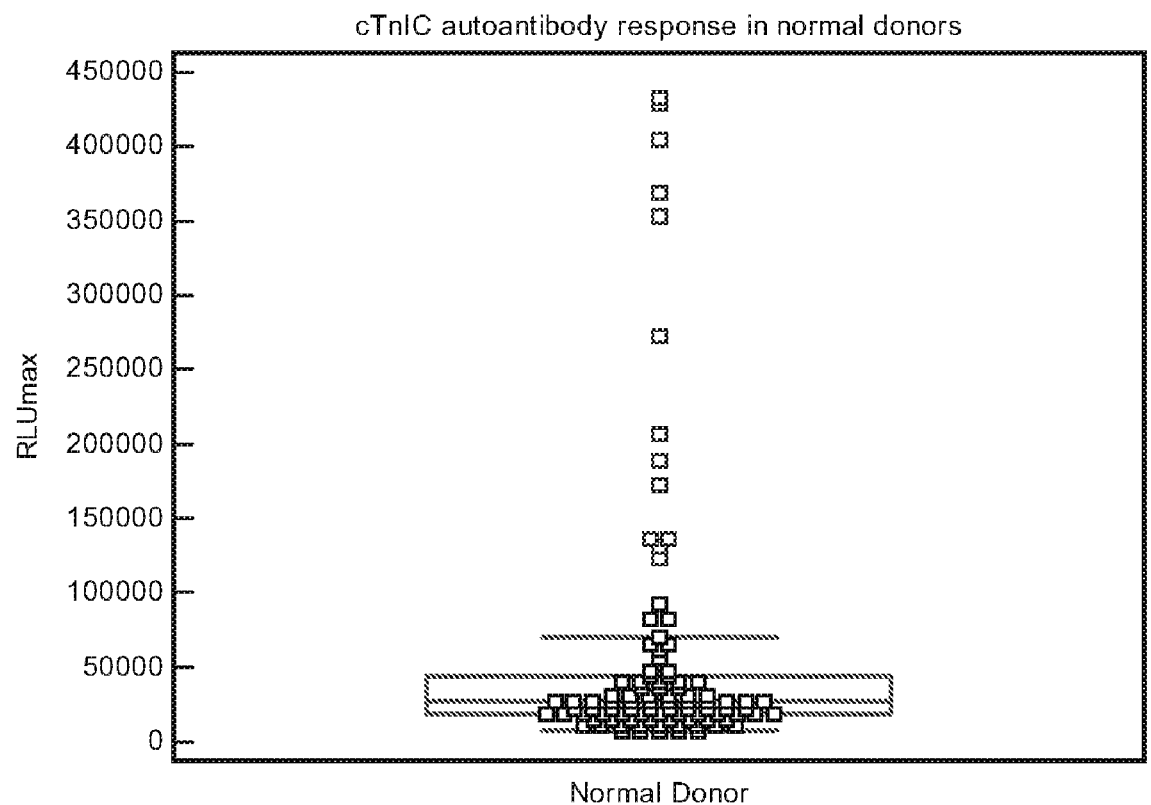
FIG. 3 is a box and whiskers plot showing cTnIC autoantibody response in normal donors as described in Example 2.

The test sample (10 μL) and the ARCHITECT® STAT-troponin I kit Preincubation Diluent (90 μL) were mixed and added to the well of a microplate coated with cTnIC at a concentration of 2000 ng/mL (Example 1.) After all test samples were dispensed, the microplate was then sealed, placed on an orbital shaker at 28 rpm and incubated at 37° C. for 2 h. The diluted test sample solutions were then removed and the wells of the microplate were washed with the ARCHITECT® Line Diluent (3×300 μl). A mouse anti-human IgG acridinium labeled conjugate solution (100 μL) was added to each test well. After the conjugate was added to all test samples, the microplate was then sealed, placed on an orbital shaker at 28 rpm and incubated at 37° C. for 1 h. The conjugate solution was then removed and the wells of the microplate were washed with the ARCHITECT® Line Diluent (3×300 μl). The microplate was loaded into the instrument and equilibrated at 37° C. The ARCHITECT® Pre-Trigger solution (100 μL) was dispensed to each well. After the pre-trigger solution was added, the plate was shaken for 72 s. Then the ARCHITECT® Trigger solution (100 μL) was dispensed to each well and chemiluminescent signal recorded for 2 s. The distribution of autoantibody responses to cTnIC is shown in FIG. 3 and a summary of the statistics is listed in Table 2. In the box and whiskers plot in FIG. 3 (and remaining Figures herein), the horizontal line in the center of the box shows the median value; the upper and lower limits of the box show the interquartile range; and the whiskers show the minimum and maximum values for each group. Sixteen of ninety-six samples (17%) gave a response greater than the 75th percentile response (95% confidence level), and four of ninety-six (4%) gave a response greater than the 90th percentile response (95% confidence level) of the total normal population.

TABLE 2

SUMMARY STATISTICS FOR cTnIC AUTOANTIBODY RESPONSE IN NORMAL DONORS

| Variable | RLUmax | |
|---|---|---|
| Sample size | 96 | |
| Lowest value | 7430 | |
| Highest value | 433140 | |
| Median | 27085 | |
| 95% Confidence Interval for the median | 23384 to 30790 | |
| Percentiles | RLUmax | 95% Confidence Interval |
| 2.5 | 10325 | |
| 25 | 18880 | 15265 to 21334 |
| 75 | 44470 | 33943 to 82256 |
| 90 | 139593 | 67033 to 359587 |
| 97.5 | 407720 | |

Example 3

Analysis of cTnI Positive Human Plasma for cTnIC Reactive Autoantibodies

Figure 4:
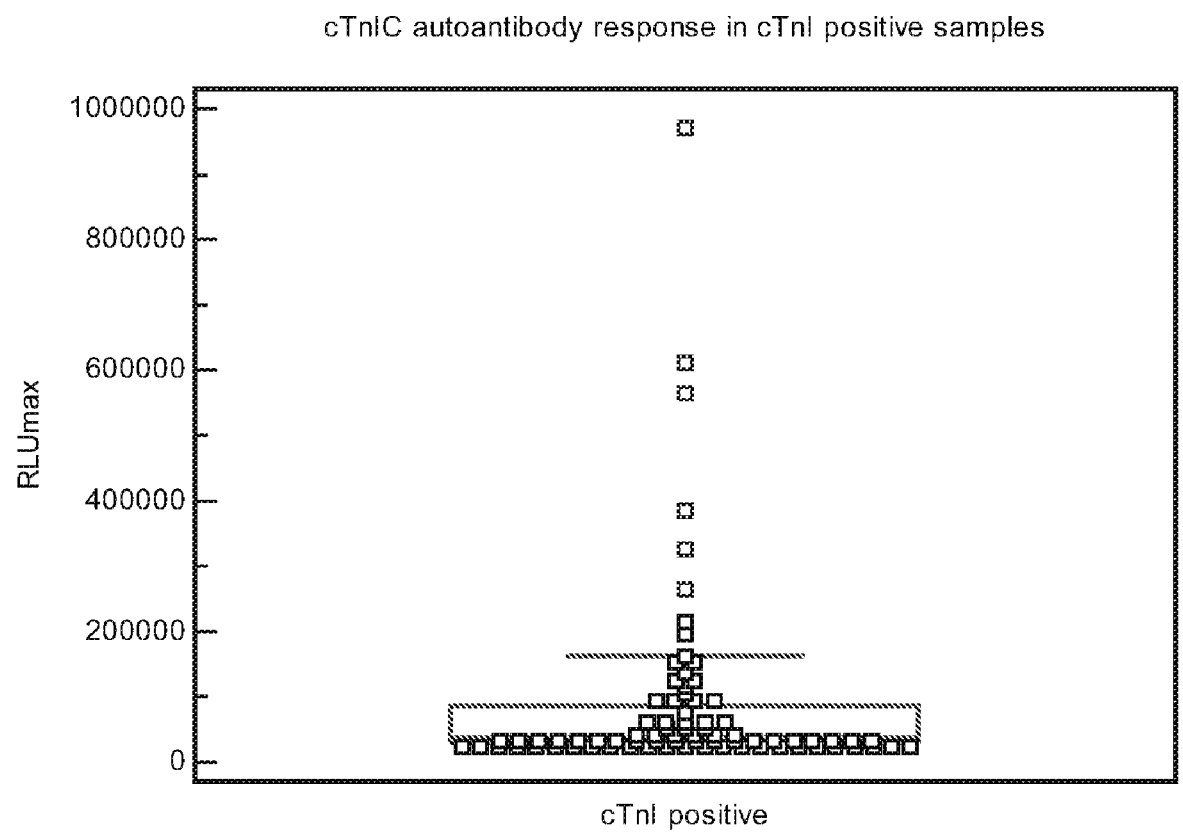
FIG. 4 is a box and whiskers plot showing cTnIC autoantibody response in cTnI positive samples as described in Example 3.

Following Example 2, human plasma samples that had tested positive for cTnI (0.2-7 ng/mL) were analyzed for cTnIC reactive autoantibodies. The distribution of autoantibody responses to cTnIC is shown in FIG. 4, and a summary of the statistics is listed in Table 3. Twelve of eighty samples (15%) gave a response greater than the 75th percentile response (95% confidence level), and 3 of eighty (4%) gave a response greater than the 90th percentile response (95% confidence level) of the total cTnI positive population.

TABLE 3

SUMMARY STATISTICS FOR cTnIC AUTOANTIBODY RESPONSE IN cTnIC POSITIVE SAMPLES

| Variable | RLUmax | |
|---|---|---|
| Sample size | 80 | |
| Lowest value | 24420 | |
| Highest value | 970910 | |
| Median | 37390 | |
| 95% Confidence Interval for the median | 33136 to 47912 | |
| Percentiles | RLUmax | 95% Confidence Interval |
| 2.5 | 25105 | |
| 25 | 30215 | 29202 to 32865 |
| 75 | 84935 | 49435 to 132933 |
| 90 | 180220 | 105752 to 468303 |
| 97.5 | 588320 | |

Example 4

Analysis of cTnI Positive Human Plasma for cTnIC Reactive IgM Autoantibodies

Figure 5:
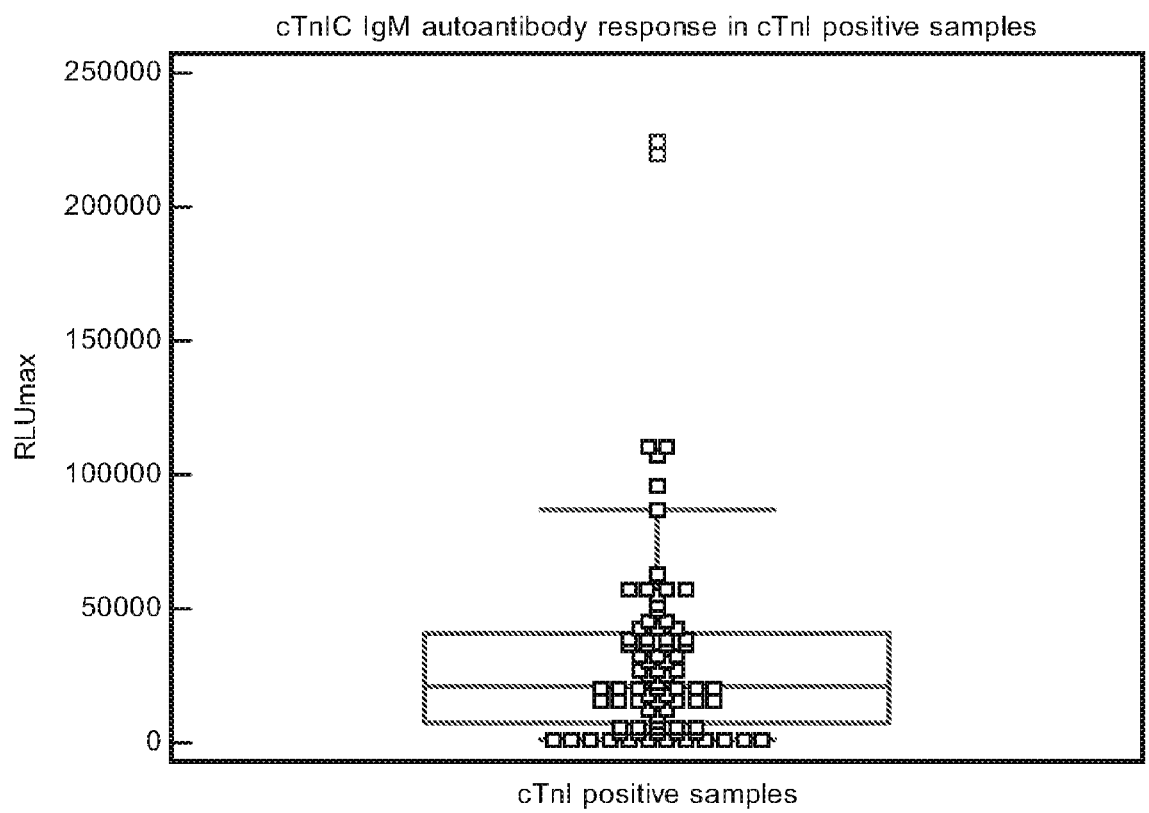
FIG. 5 is a box and whiskers plot showing cTnIC IgM autoantibody response in cTnI positive samples as described in Example 4.

Following Example 2, human plasma samples that had tested positive for cTnI (0.2-7 ng/mL) were analyzed for cTnIC reactive IgM autoantibodies. An anti-human IgM acridinium labeled conjugate solution (100 µL) was substituted for the anti-human IgG acridinium labeled conjugate solution used in Example 2. The distribution of autoantibody responses to cTnIC is shown in FIG. 5, and a summary of the statistics is listed in Table 4. Eleven of eighty samples (14%) gave a response greater than the 75th percentile response (95% confidence level), and two of eighty (3%) gave a response greater than the 90th percentile response (95% confidence level) of the total cTnI positive population.

TABLE 4

SUMMARY STATISTICS FOR cTnIC IGM AUTOANTIBODY RESPONSE IN cTnIC POSITIVE SAMPLES

| Variable | RLUmax | |
|---|---|---|
| Sample size | 80 | |
| Lowest value | 950 | |
| Highest value | 224320 | |
| Median | 21030 | |
| 95% Confidence Interval for the median | 17230 to 31797 | |
| Percentiles | RLUmax | 95% Confidence Interval |
| 2.5 | 991 | |
| 25 | 7117 | 3744 to 17106 |
| 75 | 40827 | 32999 to 55377 |
| 90 | 60332 | 46281 to 110702 |
| 97.5 | 162744 | |

Example 5

Cardiac Troponin-I Microplate Preparation

Human cardiac troponin-I (cTnI) microplates were prepared according to Example 1 using a coating concentration of 4000 ng/mL.

Example 6

Cardiac Troponin-T Microplate Preparation

Human cardiac troponin-T (cTnT) microplates were prepared according to Example 1 using a coating concentration of 4000 ng/mL.

Example 7

Cardiac Troponin-C Microplate Preparation

Human cardiac troponin-C (cTnC) microplates were prepared according to Example 1 using a coating concentration of 4000 ng/mL.

Example 8

Analysis of Normal Donor Human Plasma for cTnI Reactive Autoantibodies

Figure 6:
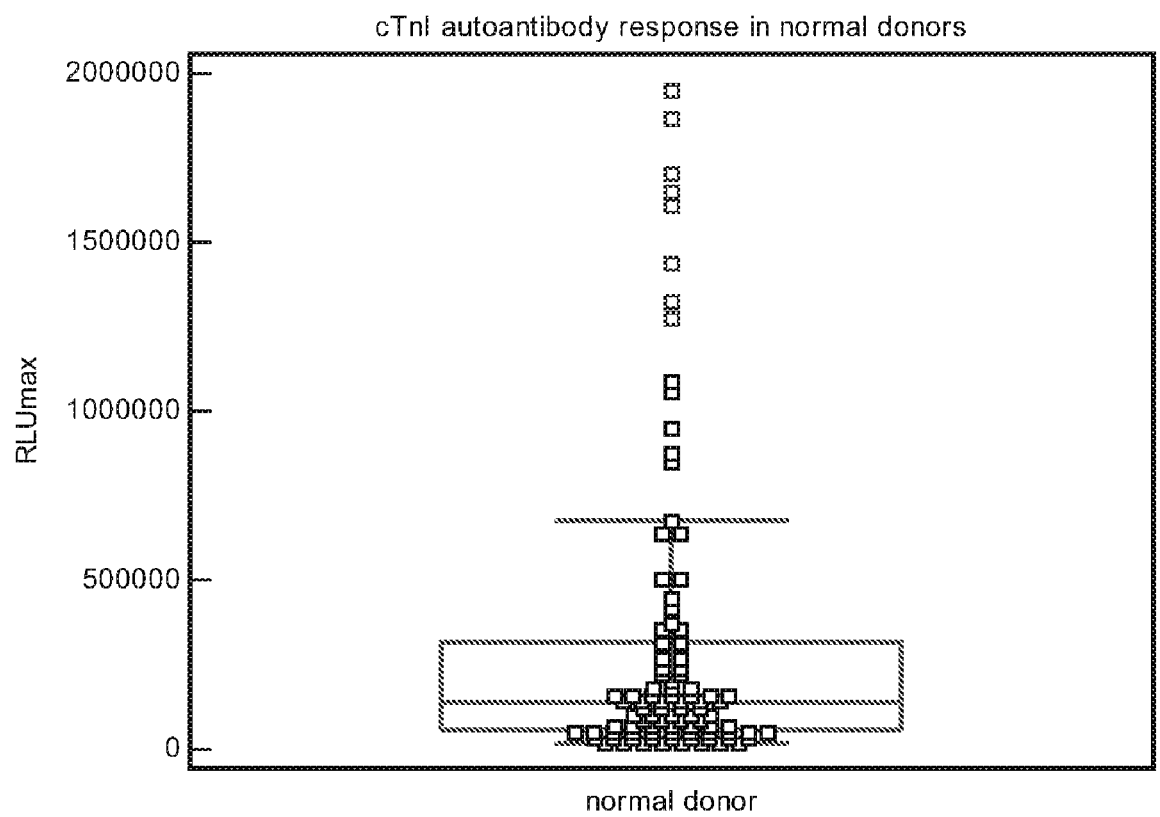
FIG. 6 is a box and whiskers plot showing cTnI autoantibody response in normal donors as described in Example 8.

Following Example 2, normal donor human plasma samples were analyzed for cTnI reactive autoantibodies using the cTnI coated microplate of Example 5. The distribution of autoantibody responses to cTnIC is shown in FIG. 6, and a summary of the statistics is listed in Table 5.

TABLE 5

SUMMARY STATISTICS OF cTnI AUTOANTIBODY RESPONSE IN NORMAL DONORS

| Variable | RLUmax | |
|---|---|---|
| Sample size | 96 | |
| Lowest value | 18650 | |
| Highest value | 1948420 | |
| Median | 137050 | |
| 95% Confidence Interval for the median | 94189 to 165093 | |

| Percentiles | RLUmax | 95% Confidence Interval |
|---|---|---|
| 2.5 | 21522 | |
| 25 | 58665 | 45176 to 79719 |
| 75 | 317435 | 181087 to 631174 |
| 90 | 1047190 | 499177 to 1622675 |
| 97.5 | 1719888 | |

Example 9

Analysis of Normal Donor Human Plasma for cTnT Reactive Autoantibodies

Figure 7:
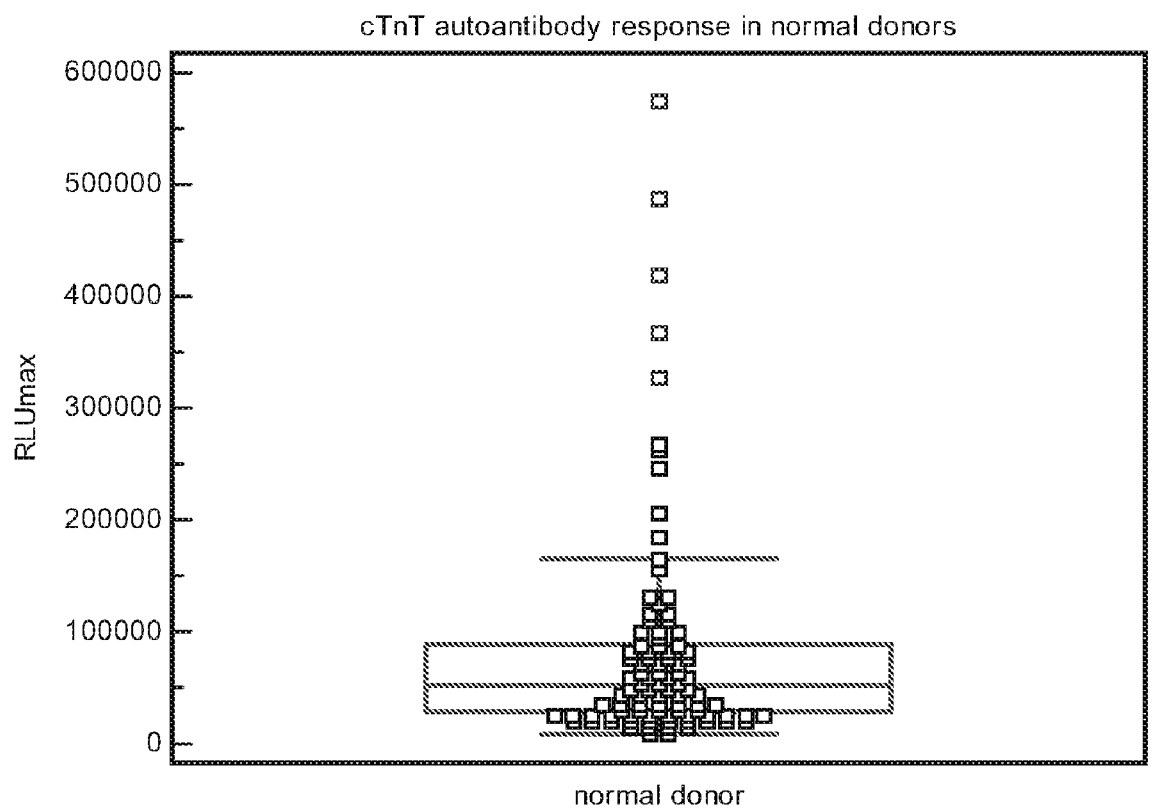
FIG. 7 is a box and whiskers plot showing cTnT autoantibody response in normal donors as described in Example 9.

Following Example 2, normal donor human plasma samples were analyzed for cTnT reactive autoantibodies using the cTnT coated microplate of example 6. The distribution of autoantibody responses to cTnT is shown in FIG. 7, and a summary of the statistics is listed in Table 6.

TABLE 6

SUMMARY STATISTICS OF cTnT AUTOANTIBODY RESPONSE IN NORMAL DONORS

| Variable | RLUmax | |
|---|---|---|
| Sample size | 96 | |
| Lowest value | 8990 | |
| Highest value | 575320 | |
| Median | 52485 | |
| 95% Confidence Interval for the median | 37119 to 67612 | |

| Percentiles | RLUmax | 95% Confidence Interval |
|---|---|---|
| 2.5 | 14379 | |
| 25 | 28165 | 23660 to 34926 |
| 75 | 89175 | 74524 to 117824 |
| 90 | 182951 | 111178 to 342099 |
| 97.5 | 425589 | |

Example 10

Analysis of Normal Donor Human Plasma for cTnC Reactive Autoantibodies

Figure 8:
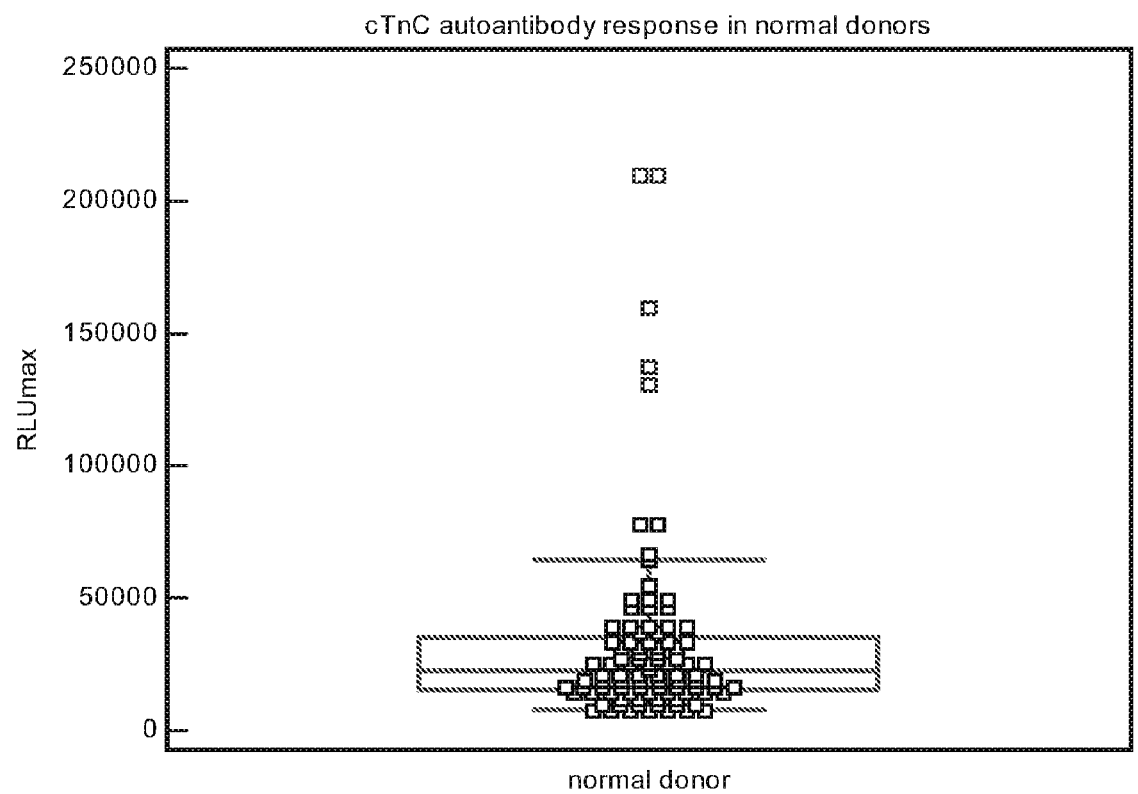
FIG. 8 is a box and whiskers plot showing cTnC autoantibody response in normal donors as described in Example 10.

Following Example 2, normal donor human plasma samples were analyzed for cTnC reactive autoantibodies using the cTnC coated microplate of example 7. The distribution of autoantibody responses to cTnC is shown in FIG. 8, and a summary of the statistics is listed in Table 7.

TABLE 7

SUMMARY STATISTICS FOR cTnC AUTOANTIBODY RESPONSE IN NORMAL DONORS

| Variable | RLUmax | |
|---|---|---|
| Sample size | 96 | |
| Lowest value | 7690 | |
| Highest value | 211150 | |
| Median | 22780 | |
| 95% Confidence Interval for the median | 19234 to 27599 | |

| Percentiles | RLUmax | 95% Confidence Interval |
|---|---|---|
| 2.5 | 8468 | |
| 25 | 15320 | 12710 to 18066 |
| 75 | 35135 | 29408 to 46244 |
| 90 | 54465 | 39834 to 133271 |
| 97.5 | 164754 | |

Example 11

Analysis of cTnI Positive Human Plasma for cTnI Reactive Autoantibodies

Figure 9:
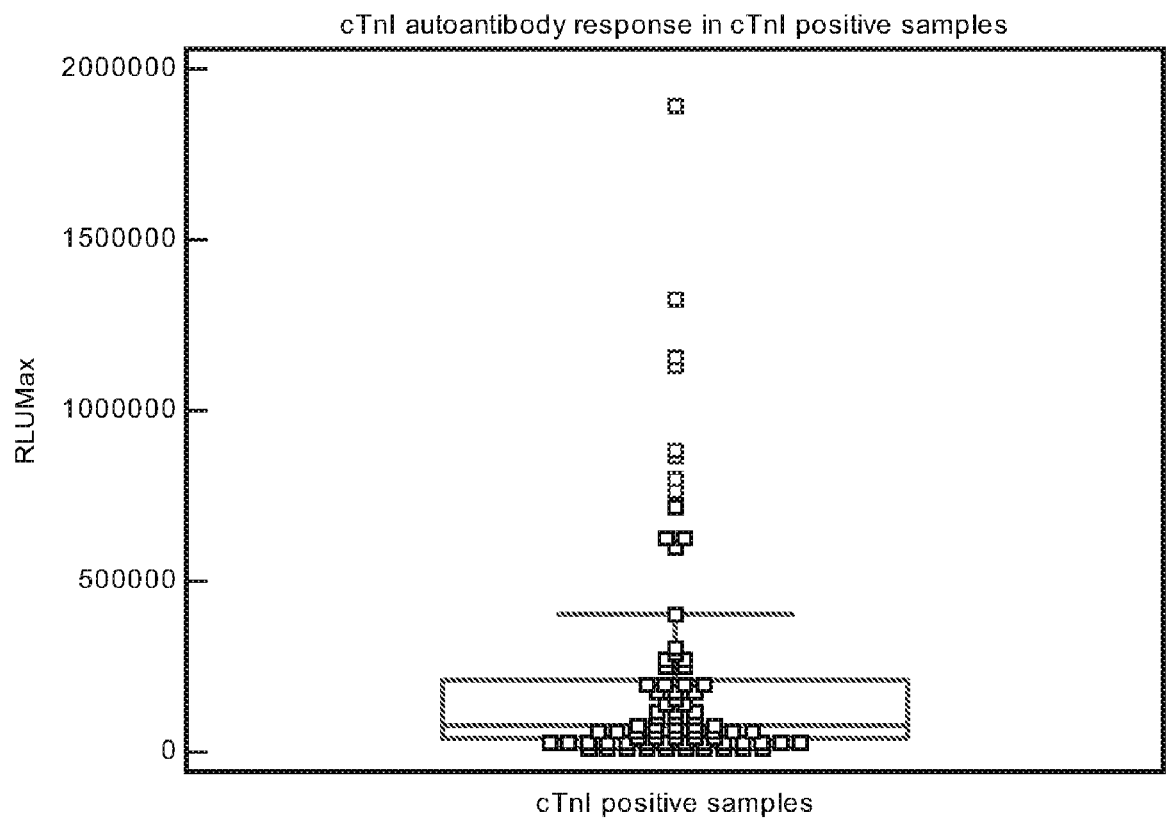
FIG. 9 is a box and whiskers plot showing cTnI autoantibody response in cTnI positive samples as described in Example 11.

Following example 2, human plasma samples that had tested positive for cTnI (0.2-7 ng/mL) were analyzed for cTnI reactive autoantibodies using the cTnI coated microplate of example 5. The distribution of autoantibody responses to cTnI is shown in FIG. 9, and a summary of the statistics is listed in Table 8.

TABLE 8

SUMMARY STATISTICS FOR cTnI AUTOANTIBODY RESPONSE IN cTnI POSITIVE SAMPLES

| Variable | RLUmax | |
|---|---|---|
| Sample size | 78 | |
| Lowest value | 10850 | |
| Highest value | 1894260 | |
| Median | 77165 | |
| 95% Confidence Interval for the median | 62609 to 132001 | |

| Percentiles | RLUmax | 95% Confidence Interval |
|---|---|---|
| 2.5 | 14403 | |
| 25 | 40430 | 29874 to 59479 |
| 75 | 210100 | 138200 to 524083 |
| 90 | 748902 | 281929 to 1147222 |
| 97.5 | 1250303 | |

Example 12

Analysis of cTnI Positive Human Plasma for cTnT Reactive Autoantibodies

Figure 10:
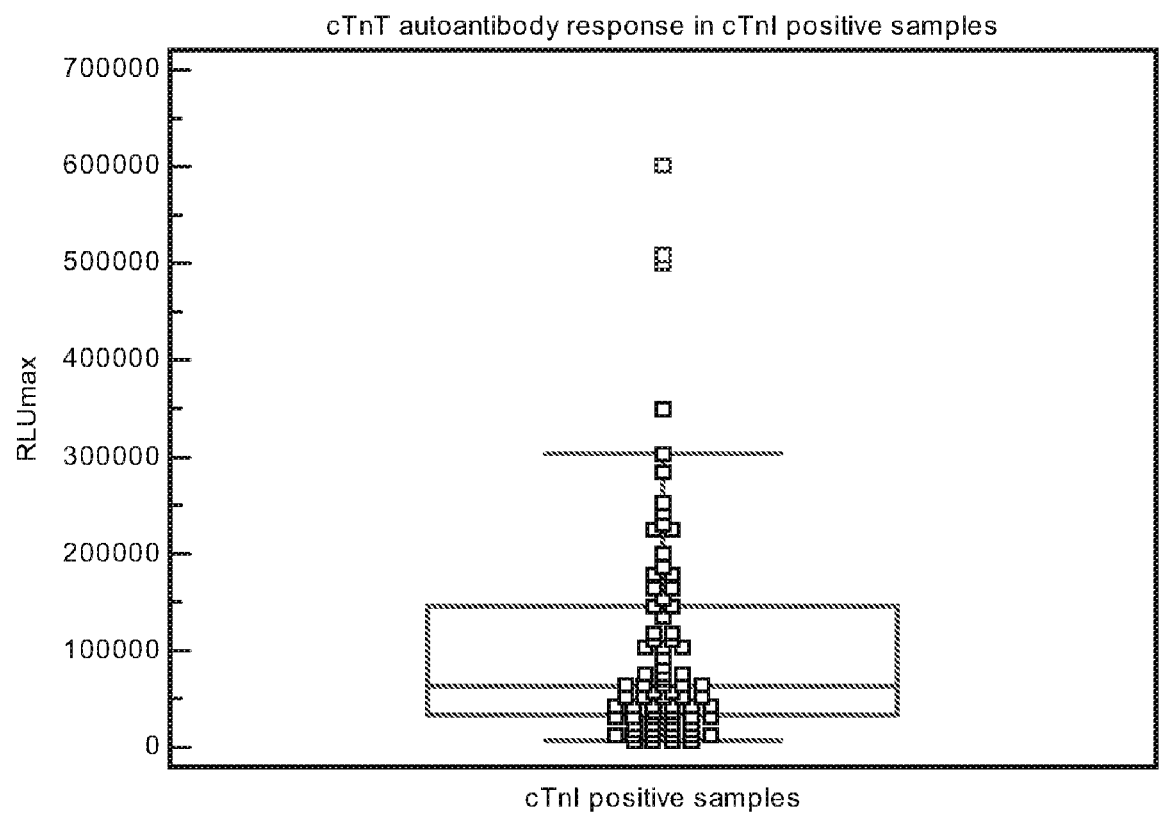
FIG. 10 is a box and whiskers plot showing cTnT autoantibody response in cTnI positive samples as described in Example 12.

Following Example 2, human plasma samples that had tested positive for cTnI (0.2-7 ng/mL) were analyzed for cTnT reactive autoantibodies using the cTnT coated microplate of example 6. The distribution of autoantibody responses to cTnT is shown in FIG. 10, and a summary of the statistics is listed in Table 9.

TABLE 9

SUMMARY STATISTICS FOR cTnT AUTOANTIBODY RESPONSE IN cTnI POSITIVE SAMPLES

| Variable | RLUmax | |
|---|---|---|
| Sample size | 78 | |
| Lowest value | 7490 | |
| Highest value | 601320 | |
| Median | 63055 | |
| 95% Confidence Interval for the median | 46113 to 84008 | |

| Percentiles | RLUmax | 95% Confidence Interval |
|---|---|---|
| 2.5 | 8429 | |
| 25 | 33490 | 19615 to 44224 |
| 75 | 145390 | 92096 to 195389 |
| 90 | 239905 | 171920 to 438160 |
| 97.5 | 505160 | |

Example 13

Analysis of cTnI Positive Human Plasma for cTnC Reactive Autoantibodies

Figure 11:
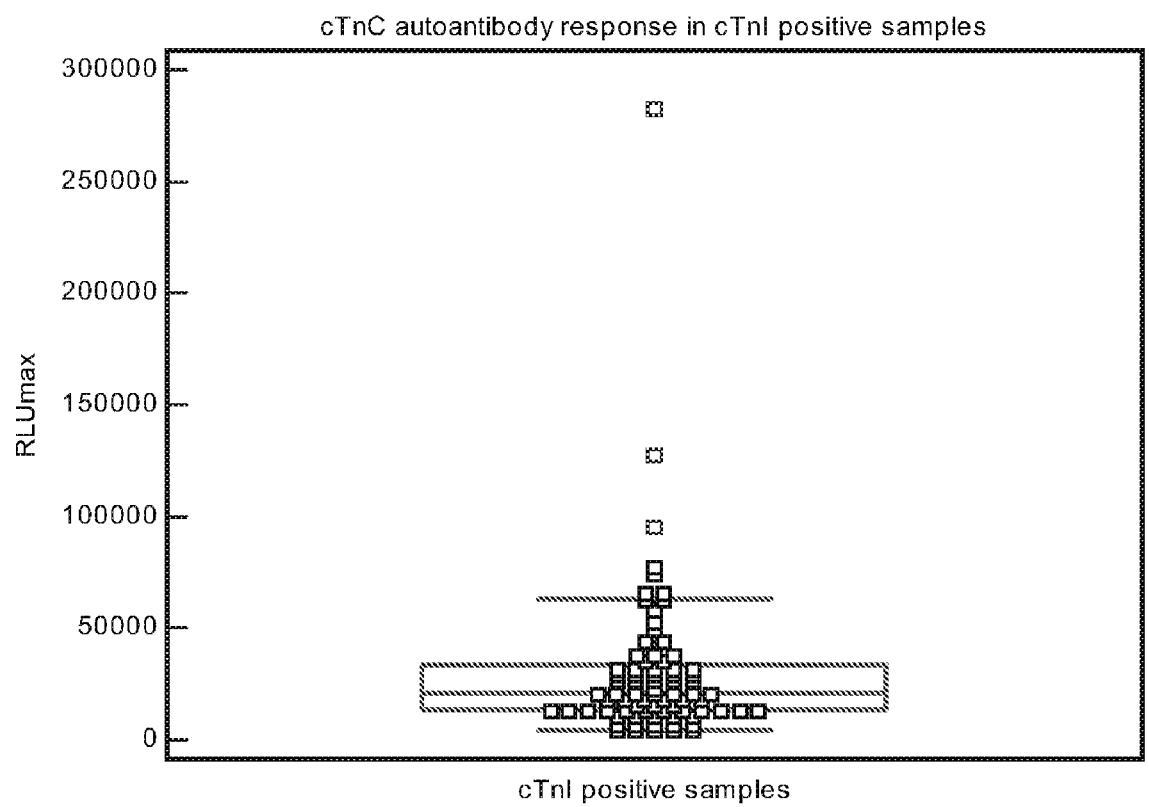
FIG. 11 is a box and whiskers plot showing cTnC autoantibody response in cTnI positive samples as described in Example 13.

Following Example 2, human plasma samples that had tested positive for cTnI (0.2-7 ng/mL) were analyzed for cTnC reactive autoantibodies using the cTnC coated microplate of Example 7. The distribution of autoantibody responses to cTnC is shown in FIG. 11 and a summary of the statistics is listed in Table 10.

TABLE 10

SUMMARY STATISTICS FOR cTnC AUTOANTIBODY RESPONSE IN cTnI POSITIVE SAMPLES

| Variable | RLUmax | |
|---|---|---|
| Sample size | 78 | |
| Lowest value | 4510 | |
| Highest value | 282950 | |
| Median | 21130 | |
| 95% Confidence Interval for the median | 16929 to 28801 | |

| Percentiles | RLUmax | 95% Confidence Interval |
|---|---|---|
| 2.5 | 6147 | |
| 25 | 13690 | 11331 to 16786 |
| 75 | 33690 | 29316 to 47631 |
| 90 | 63072 | 38786 to 87788 |
| 97.5 | 112987 | |

Example 13

Figure 12:
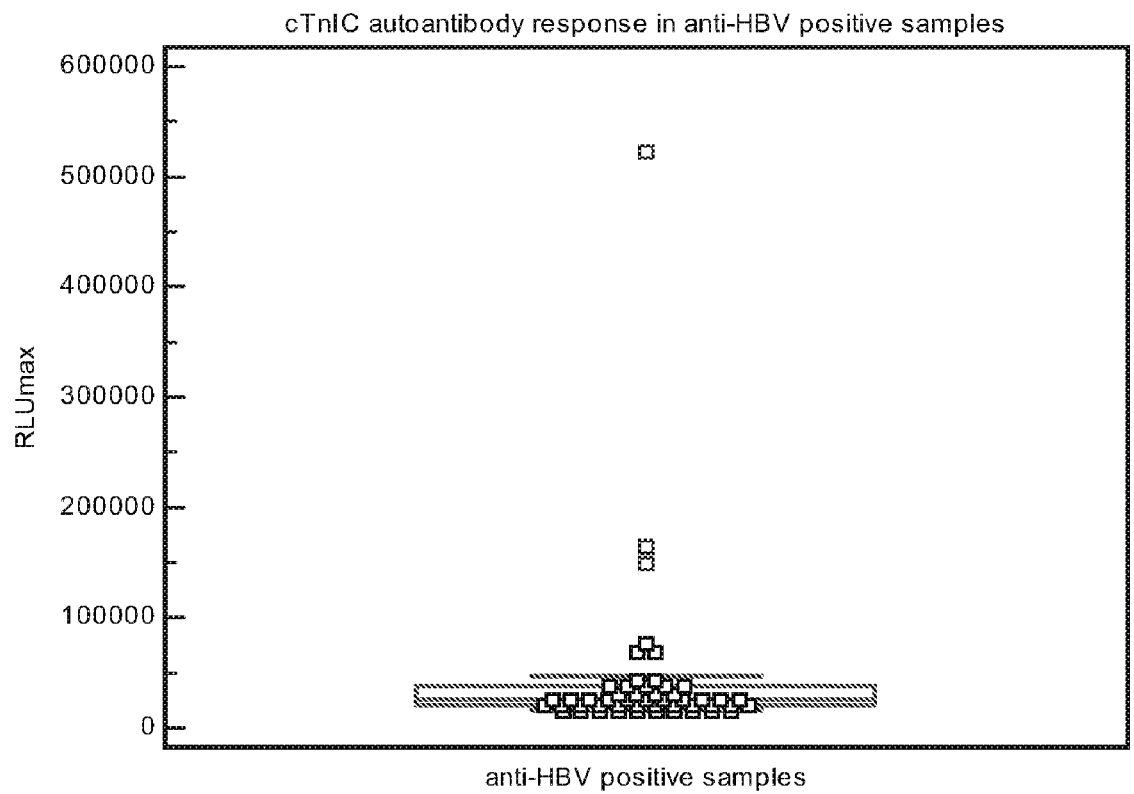
FIG. 12 is a box and whiskers plot showing cTnIC autoantibody response in anti-HBV positive samples as described in Example 14.

Analysis of Anti-HBV Positive Human Plasma for cTnIC Reactive Autoantibodies Following Example 2, human plasma samples that had tested positive for hepatitis B viral antibody from natural infection were analyzed for cTnIC reactive autoantibodies using the cTnIC coated microplate of Example 1. The distribution of autoantibody responses to cTnIC is shown in FIG. 12, and a summary of the statistics is listed in Table 11.

TABLE 11

SUMMARY STATISTICS FOR cTnIC AUTOANTIBODY RESPONSE IN ANTI-HBV POSITIVE SAMPLES

| Variable | RLUmax | |
|---|---|---|
| Sample size | 50 | |
| Lowest value | 15960 | |
| Highest value | 522730 | |
| Median | 26075 | |
| 95% Confidence Interval for the median | 24010 to 30057 | |

| Percentiles | RLUmax | 95% Confidence Interval |
|---|---|---|
| 2.5 | 16057 | |
| 25 | 21560 | 19566 to 24825 |
| 75 | 38510 | 28538 to 48317 |
| 90 | 71180 | 39455 to 278536 |
| 97.5 | 254387 | |

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention. All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of determining the reliability of a cardiac troponin antigen assay in a biological sample from a subject, the method comprising
    assaying the biological sample from the subject for an autoantibody reactive with the cardiac troponin antigen being assayed, to allow detection of an elevated level of the cardiac troponin-reactive autoantibody against the cardiac troponin antigen in the biological sample in comparison to a predetermined normal control sample having normal values of cardiac troponin-reactive autoantibody against the cardiac troponin antigen, wherein assaying comprises
  (a) contacting the biological sample with a cardiac troponin antigen, under conditions sufficient for binding of the cardiac troponin antigen to any corresponding cardiac troponin-reactive autoantibody present in the sample;
  (b) contacting the biological sample with a labeled cardiac troponin-reactive antibody under conditions sufficient for the labeled cardiac troponin-reactive antibody to compete with said cardiac troponin-reactive autoantibody for specific binding to the cardiac troponin antigen; and
  (c) detecting the level of complex(es) comprising the cardiac troponin antigen bound to the labeled cardiac troponin-reactive antibody, wherein the level of said complex(es) is negatively correlated with the level of the corresponding cardiac troponin-reactive autoantibody present in the sample; and wherein:
    detecting an elevated level of cardiac troponin-reactive autoantibody in the biological sample in comparison to the predetermined normal control sample provides indication that the biological sample is scored as one in which the cardiac troponin antigen assay is not reliable, and
    detecting a level of cardiac troponin-reactive autoantibody that is not elevated in the biological sample in comparison to the predetermined normal control sample provides indication that the biological sample is scored as one in which the cardiac troponin antigen assay is reliable.

2. The method of claim 1, wherein the biological sample is obtained from a human.

3. The method of claim 1, wherein the cardiac troponin antigen assayed comprises a cardiac troponin antigen selected from the group consisting of a cardiac troponin I, cardiac troponin T, and cardiac troponin C, and complexes thereof.

4. The method of claim 1, wherein the autoantibody is reactive with a cardiac troponin antigen comprising a cardiac troponin antigen selected from the group consisting of a cardiac troponin I, cardiac troponin T, and cardiac troponin C, and complexes thereof.

5. The method of claim 1, wherein the method is carried out before, or simultaneously with, the cardiac troponin antigen assay.

6. The method of claim 1, wherein the method is carried out in the absence of the cardiac troponin antigen assay.

7. The method of claim 1, wherein the sample is determined to have an elevated level of cardiac troponin-reactive autoantibody, and the sample is assessed for one or more additional indicators of cardiac pathology selected from the group consisting of myoglobin, CK-MB, BNP, CRP, Troponin-I, Troponin-T, blood oxygen level, cardiac imaging, and electrocardiography.

8. The method of claim 1, wherein the contacting of claim 1(a) and the contacting of claim 1(b) are carried out simultaneously.

9. The method of claim 1, wherein the contacting of claim 1(a) and the contacting of claim 1(b) are carried out sequentially, in any order.

10. The method of claim 1, wherein the cardiac troponin antigen is affixed to a solid phase, binding of the cardiac troponin antigen to labeled cardiac troponin-reactive antibody or to the corresponding cardiac troponin-reactive autoantibody present in the sample forms a solid phase-affixed complex, and said detecting comprises detecting a signal from the solid phase-affixed complex.

11. The method of claim 10, wherein the solid phase comprises a microparticle.

12. The method of claim 10, wherein the solid phase comprises an electrode.

13. The method of claim 1, wherein the label comprises a direct label.

14. The method of claim 13, wherein the direct label comprises an acridinium-9-carboxamide.

15. The method of claim 1, wherein the label comprises an indirect label.

16. The method of claim 1, wherein the detecting of (c) comprises contacting the label with an indicator reagent.

17. A test kit for use in assaying a biological sample from a human for an autoantibody reactive with a cardiac troponin antigen, the test kit comprising a humanized monoclonal antibody, wherein the humanized monoclonal antibody is specific for a cardiac Troponin-I or Troponin-T, wherein the test kit additionally comprises a solid phase and a capture agent affixed to the solid phase, wherein the capture agent is selected from the group consisting of a cardiac troponin antigen and a human-specific antibody which binds to the cardiac troponin-reactive autoantibody against the cardiac troponin antigen, and wherein, if the capture agent comprises a cardiac troponin antigen, the kit additionally comprises a human-specific antibody which binds to the cardiac troponin-reactive autoantibody against the cardiac troponin antigen.

18. The test kit of claim 17, wherein the test kit additionally comprises a labeled detection agent, wherein
  if the capture agent comprises a cardiac troponin antigen, the detection agent comprises the human-specific antibody; and
  if the capture agent comprises a human-specific antibody, the detection agent comprises a cardiac troponin antigen.

19. The test kit of claim 18, wherein at least the label comprises a direct label.

20. The test kit of claim 19, wherein the direct label comprises an acridinium-9-carboxamide.

21. The test kit of claim 18, wherein the label comprises an indirect label.

22. The test kit of claim 18, additionally comprising an indicator reagent that interacts with at least one label to produce a detectable signal.

23. The test kit of claim 17, wherein the solid phase comprises a microplate.

24. The test kit of claim 17, wherein the solid phase comprises a microparticle.

25. The test kit of claim 17, wherein the solid phase comprises an electrode.

26. A test kit for use in assaying a biological sample from a human for an autoantibody reactive with a cardiac troponin antigen, the test kit comprising a humanized monoclonal antibody, wherein the humanized monoclonal antibody is specific for a cardiac Troponin-I or Troponin T, wherein the test kit additionally comprises a labeled non-human monoclonal antibody, wherein the non-human monoclonal antibody is specific for a cardiac Troponin-I or Troponin-T, and a human-specific antibody which binds to the cardiac troponin-reactive autoantibody against the cardiac troponin antigen.

* * * * *